United States Patent

Mochida et al.

[11] Patent Number: 5,489,985
[45] Date of Patent: Feb. 6, 1996

[54] APPARATUS FOR INSPECTION OF PACKAGED PRINTED CIRCUIT BOARDS

[75] Inventors: Shohroh Mochida, Hirakata; Tomohiro Kimura, Ehime; Osamu Yamada, Matsuyama; Yuji Ono, Ehime; Hidenori Nagata, Matsuyama, all of Japan

[73] Assignee: Matsushita Electric Industrial Co., Ltd., Osaka, Japan

[21] Appl. No.: 181,586

[22] Filed: Jan. 14, 1994

[30] Foreign Application Priority Data

| Jan. 21, 1993 | [JP] | Japan | 5-008105 |
| Jan. 22, 1993 | [JP] | Japan | 5-008783 |
| Jan. 22, 1993 | [JP] | Japan | 5-008784 |
| Jan. 22, 1993 | [JP] | Japan | 5-008785 |
| Jan. 22, 1993 | [JP] | Japan | 5-008977 |

[51] Int. Cl.$^6$ ............................ G01B 11/00; H01J 3/14
[52] U.S. Cl. ..................... 356/398; 356/237; 250/235; 250/559.29
[58] Field of Search ........................ 356/398, 394, 356/375, 376, 388, 237, 445, 446; 250/560, 561, 235, 236, 578.1; 359/201, 202, 205, 206, 212–219; 348/87, 125, 126

[56] References Cited

U.S. PATENT DOCUMENTS

| 3,977,789 | 8/1976 | Hunter et al. | 356/394 |
| 4,983,827 | 1/1991 | Ikegaya et al. | 250/561 |
| 5,004,929 | 4/1991 | Kakinoki et al. | 250/561 |
| 5,078,463 | 1/1992 | Kawawada | 359/201 |
| 5,200,799 | 4/1993 | Maruyama et al. | 356/394 |
| 5,329,359 | 7/1994 | Tachikawa | 356/398 |

Primary Examiner—Hoa Q. Pham
Attorney, Agent, or Firm—Stevens, Davis, Miller & Mosher

[57] ABSTRACT

There is provided an apparatus of inspecting a packaged state by scanning a packaged printed circuit board with a fine light beam and detecting reflection beams of the fine light beam in a plurality of directions. A fine light beam emitted from a light source is scanned on the packaged printed circuit board substantially vertically thereto by means of a polygon mirror and a light projection fθ lens. An optical path correcting system receives reflection beams scattered from the packaged printed circuit board and corrects optical paths of the reflection beams. The correction is done in such a way that reflection beams having constant directional vectors regardless of the change of the scanning position of the fine light beam are received and guided to light receiving positions complying with a height at a scanning position on a plurality of photoelectric conversion devices. Through this, the packaged state of parts is inspected at a high speed, with high accuracy and over a wide range without expanding the light receiving area of the photoelectric conversion device and without causing characteristics of triogonometrical survey to change with the scanning position.

25 Claims, 26 Drawing Sheets

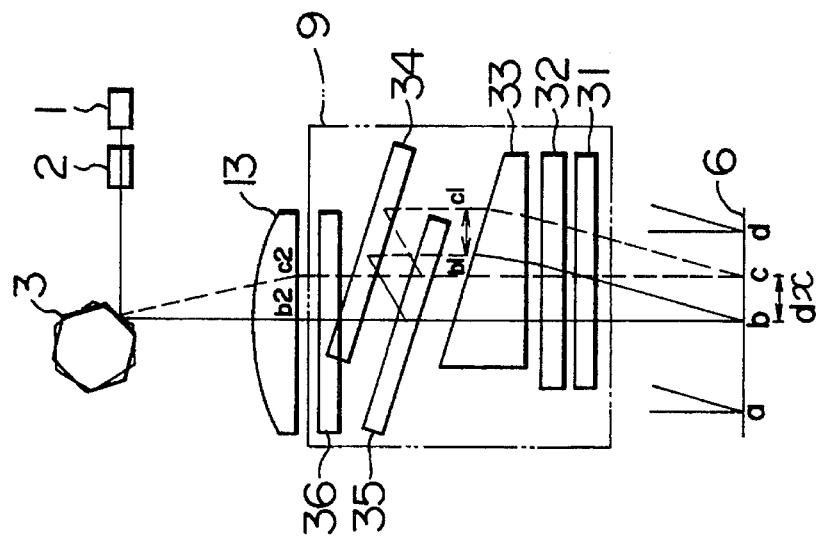
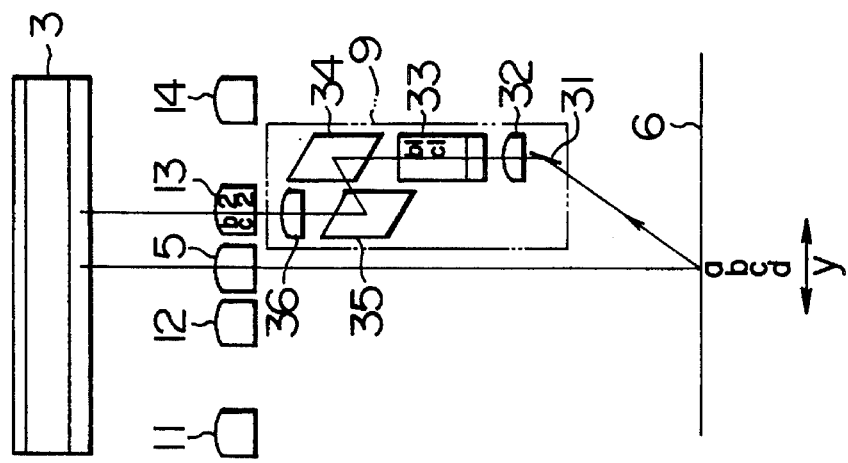

F I G. 3
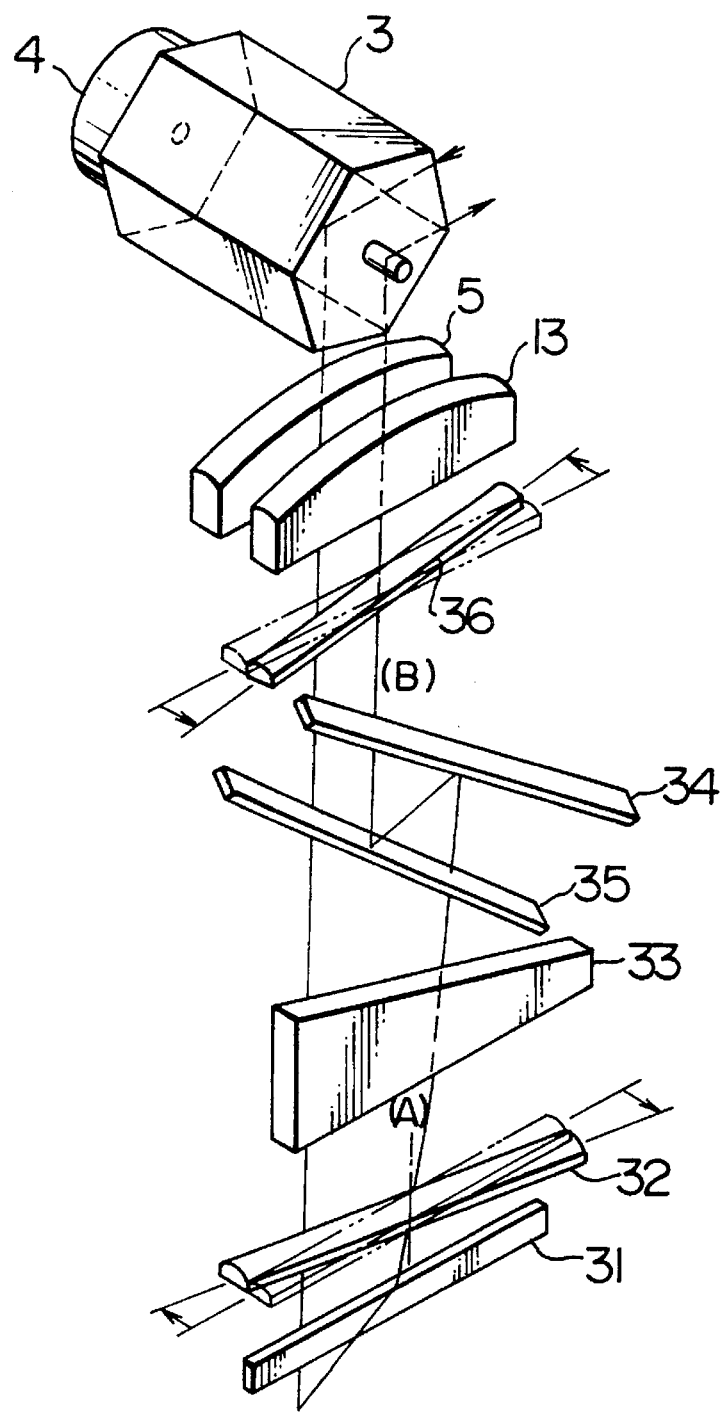

F I G. 11
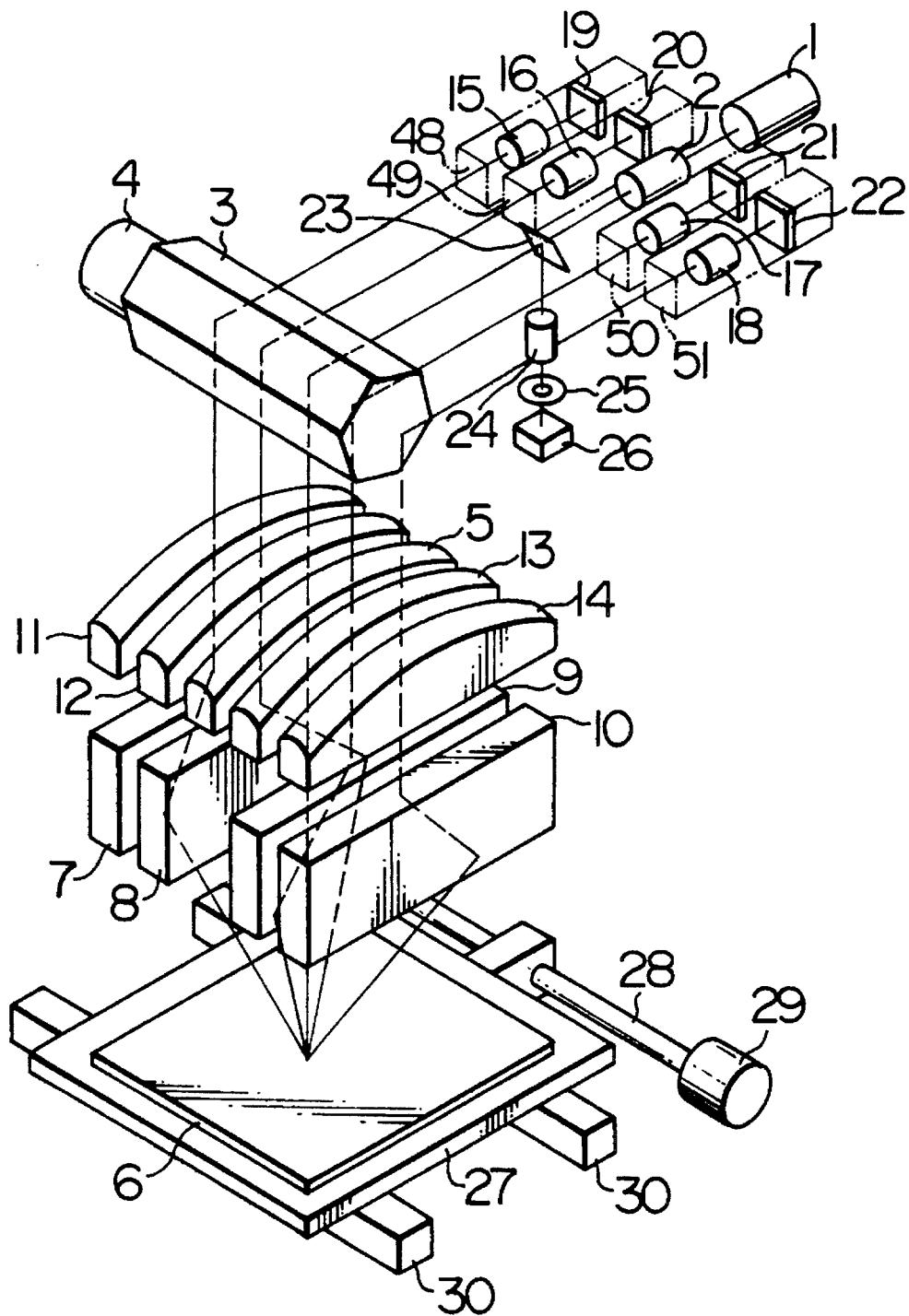

F I G. 13
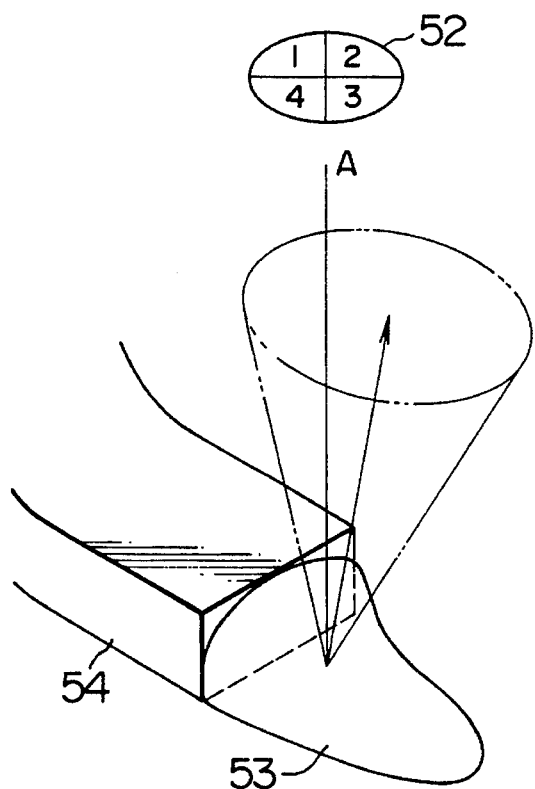
F I G. 14
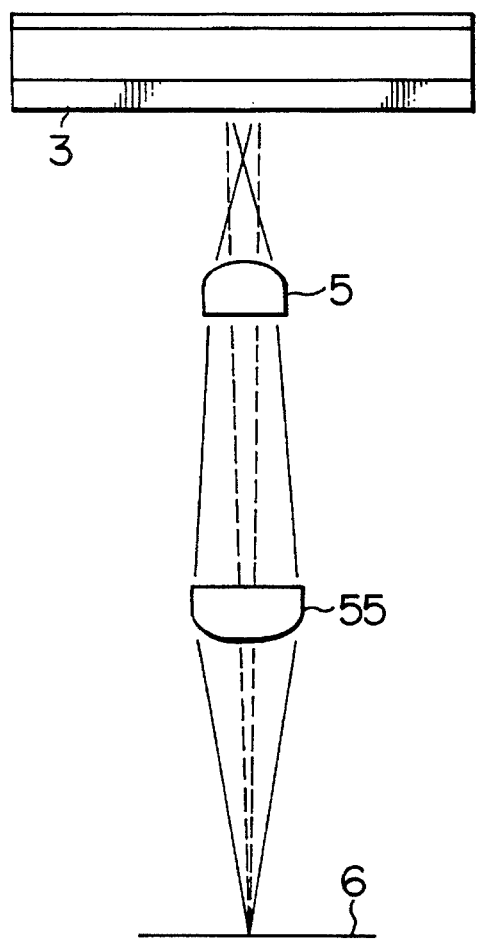

F I G. 15
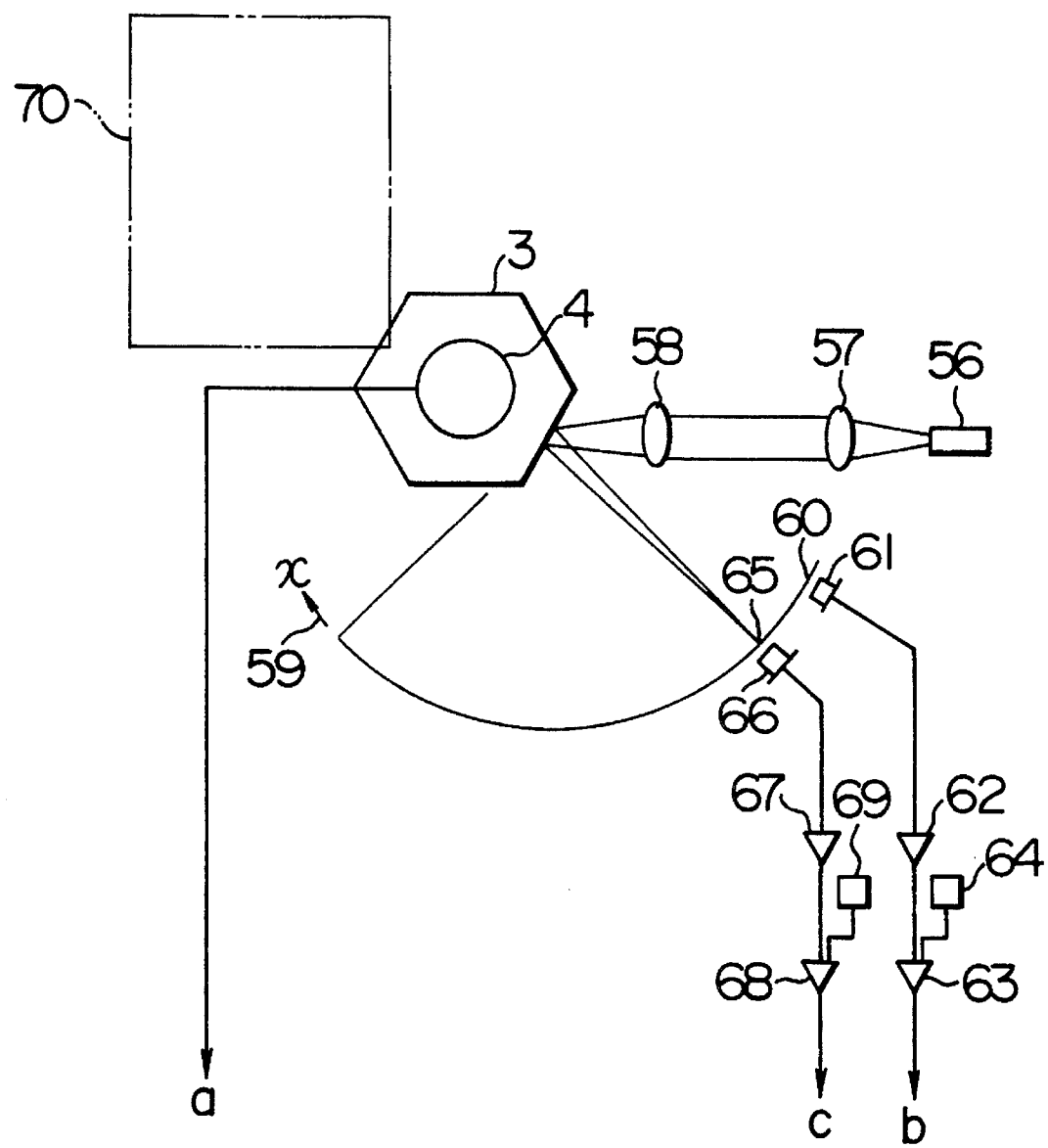

APPARATUS FOR INSPECTION OF PACKAGED PRINTED CIRCUIT BOARDS

BACKGROUND OF THE INVENTION

Field of the Invention

The present invention relates to an apparatus for inspection of packaged printed circuit boards and more particularly to a packaged printed circuit board inspection apparatus in which a fine light beam, finely focused, is irradiated on a packaged printed circuit board and reflection beams therefrom are detected by using the principle of trigonometrical survey to inspect the positional shift, loss and defective soldering of packaged parts.

Description of the Related Art

In recent years, for inspection of the positional shift, loss and defective soldering of parts of a packaged printed circuit board, a non-contact type inspection apparatus based on the principle of trigonometrical survey has been used in which a finely focused light beam is irradiated on the packaged printed circuit board and reflection beams therefrom are detected.

Prior art will be described hereunder with reference to the accompanying drawings. FIG. 25 shows an example of a conventional packaged printed circuit board inspection apparatus. In the drawings, light beams will be all represented by optical axes. In FIG. 25, a light source 120 generates a fine light beam to be irradiated on a packaged printed circuit board 126, a collimator lens system 121 converts the fine light beam into a parallel flux of light, a polygon mirror 122 deflects the parallel light flux, a projection lens system 125 irradiates the parallel light flux deflected by the polygon mirror 122 onto the packaged printed circuit board 126 vertically thereto, a mirror 124 guides the parallel light flux deflected by the polygon mirror to the projection lens system 125, light receiving lens systems 127, 128, 129 and 130 collect reflection beams from the packaged printed circuit board 126, and photoelectric conversion devices 131, 132, 133 and 134 measure light receiving positions at which the reflection beams collected by the light receiving lens systems 127, 128, 129 and 130 are received by the devices 131 to 134. A polygon motor 123 rotates the polygon mirror 122 to change the beam irradiation position of the fine light beam on the packaged printed circuit board 126, a table 135 moves the packaged printed circuit board 126 in a direction of arrow y in accordance with the optical scanning (in a direction of arrow x), a ball screw 136 is driven for rotation to move the table 135, a motor 137 rotates the ball screw 136, and guide rails 138 are adapted to guide the table 135.

The operation of the packaged printed circuit board inspection apparatus constructed as above will be described. A fine light beam emitted from the light source 120 is converted by the collimator lens system 121 into a parallel light flux which is deflected by the polygon mirror 122 and mirror 124 to pass through the projection lens system 125 and irradiate the packaged printed circuit board 126 vertically thereto. The polygon mirror 122 is driven for rotation by the polygon motor 123 and as the polygon mirror 122 rotates, the fine light beam is scanned on the packaged printed circuit board 126 in the direction of arrow x.

Reflection beams of the fine light beam which return from the packaged printed circuit board 126 are collected by the light receiving systems 127, 128, 129 and 130 arranged in four directions and are irradiated on the photoelectric conversion devices 131, 132, 133 and 134 at positions corresponding to a height of a scanning position of the fine light beam on the packaged printed circuit board 126. The irradiation positions are detected on the basis of electrical outputs of the photoelectric conversion devices 131, 132, 133 and 134 and the shape of the surface of the packaged printed circuit board is measured through the principle of trigonometrical survey. By moving the table 135 in the direction of arrow y vertical to the scanning direction by means of the motor 137, ball screw 136 and guide rails 138, the three-dimensional shape of the entire surface of the packaged printed circuit board 126 can be measured.

However, in the prior art construction as above, as the scanning position changes, the light receiving angle for the reflection beam and the collecting position for the reflection beam on the photoelectric conversion device change even when the height of an object to be measured remains unchanged. This phenomenon will be described with reference to FIG. 26. FIG. 26 is a side view of FIG. 25 as seen in the direction of arrow y, showing light receiving positions a and b for reflection beams on the photoelectric conversion devices when the scanning position changes from A to B. For simplicity of explanation, the mirror 124 is omitted. As is clear from FIG. 26, even when the same surface height is measured, the light receiving position and collecting position for the reflection beams on each of the photoelectric conversion devices change greatly as the scanning position changes.

Therefore, each of the photoelectric conversion devices 131, 132, 133 and 134 needs, in addition to a light receiving range of reflection beams necessary for height measurement, a light receiving range for covering a change in the light receiving position for reflection beams due to a change in the scanning position, and for simultaneous measurement over a wide range, photoelectric conversion devices each having a wide light receiving area are required. In general, the photoelectric conversion device has such characteristics that as the light receiving area expands, the response speed is degraded and therefore it is difficult to measure the three-dimensional shape of a measuring object of wide range at a high speed.

Further, because of the phenomenon that the light receiving position changes with the scanning position, the height must be corrected in accordance with scanning positions. Accordingly, the resolution of the sensor per se constructed of the photoelectric conversion devices and processing circuits cannot be used exclusively for height measurement and the accuracy is deteriorated.

In addition, the light receiving angle changes with the scanning position, raising a problem that characteristics of the triogonometrical survey, for example, the state of the dead angle (a portion which has an irregularity in its surface to intercept reflection beams and cannot be measured through trigonometrical survey) changes with the scanning position.

SUMMARY OF THE INVENTION

Accordingly, the present invention intends to solve the above problems and it is an object of the present invention to provide an apparatus which can acquire and inspect the three-dimensional shape of a packaged printed circuit board standing for an object to be inspected at a high speed, with high accuracy and over a wide range without being affected by the shape of the measuring object.

To accomplish the above object, a packaged printed circuit board inspection apparatus according to the present invention comprises a light source for generating a light beam which is irradiated on a packaged printed circuit board to be inspected, deflection means for deflecting the light beam generated from the light source to cause it to scan the packaged printed circuit board, a light projection lens system for irradiating the light beam deflected by the deflection means onto the packaged printed circuit board vertically thereto, a plurality of optical path correcting means for receiving some of reflection beams, scattered from an irradiation position of the light beam caused to irradiate the packaged printed circuit board vertically thereto, which have constant directional vectors relative to the optical axis of the vertically irradiated light beam regardless of the change of the scanning position of the light beam and for guiding the received reflection beams in such as way that these reflection beams become vertical to the packaged printed circuit board and parallel to a direction which is vertical to the scanning direction, a light receiving optical system for guiding, in parallel to each other, a plurality of reflection beams having passed through the plurality of optical path correcting means to the deflection means, and photoelectric conversion means for receiving the reflection beams deflected by the deflection means and converting light quantities of the received reflection beams into electrical outputs complying with a height of the light beam irradiation position on the packaged printed circuit board.

With the above construction, a fine light beam is irradiated on the packaged printed circuit board substantially vertically thereto, and reflection beams scattered from an irradiation position of the fine light beam in a plurality of mutually different directions are received at positions on the photoelectric conversion means complying with a height of an object to be measured regardless of the fine light beam irradiation position. Accordingly, the three-dimensional shape of the measuring object can be acquired by sensing from many directions reflection beams scattered from an irradiation position of the fine light beam at a high speed, with high accuracy and over a wide range without expanding the light receiving area of the photoelectric conversion means and without causing characteristics of trigonometrical survey to change with the scanning position.

BRIEF DESCRIPTION OF THE DRAWINGS

FIGS. 2A and 2B are diagrams showing the construction of an optical path correcting optical system of the apparatus;

FIG. 3 is a perspective view showing the construction of another optical path correcting optical system of the apparatus;

FIG. 11 is a perspective view useful to explain still another embodiment of the light receiving lens unit of the apparatus;

FIGS. 13 and 14 are diagrams for explaining another embodiment of the light receiving system for a reflection beam in the vertical direction;

FIG. 15 is a diagram showing the construction of an embodiment of a jitter corrector in the packaged printed circuit board according to the present invention;

DESCRIPTION OF THE PREFERRED EMBODIMENTS

Figure 1:
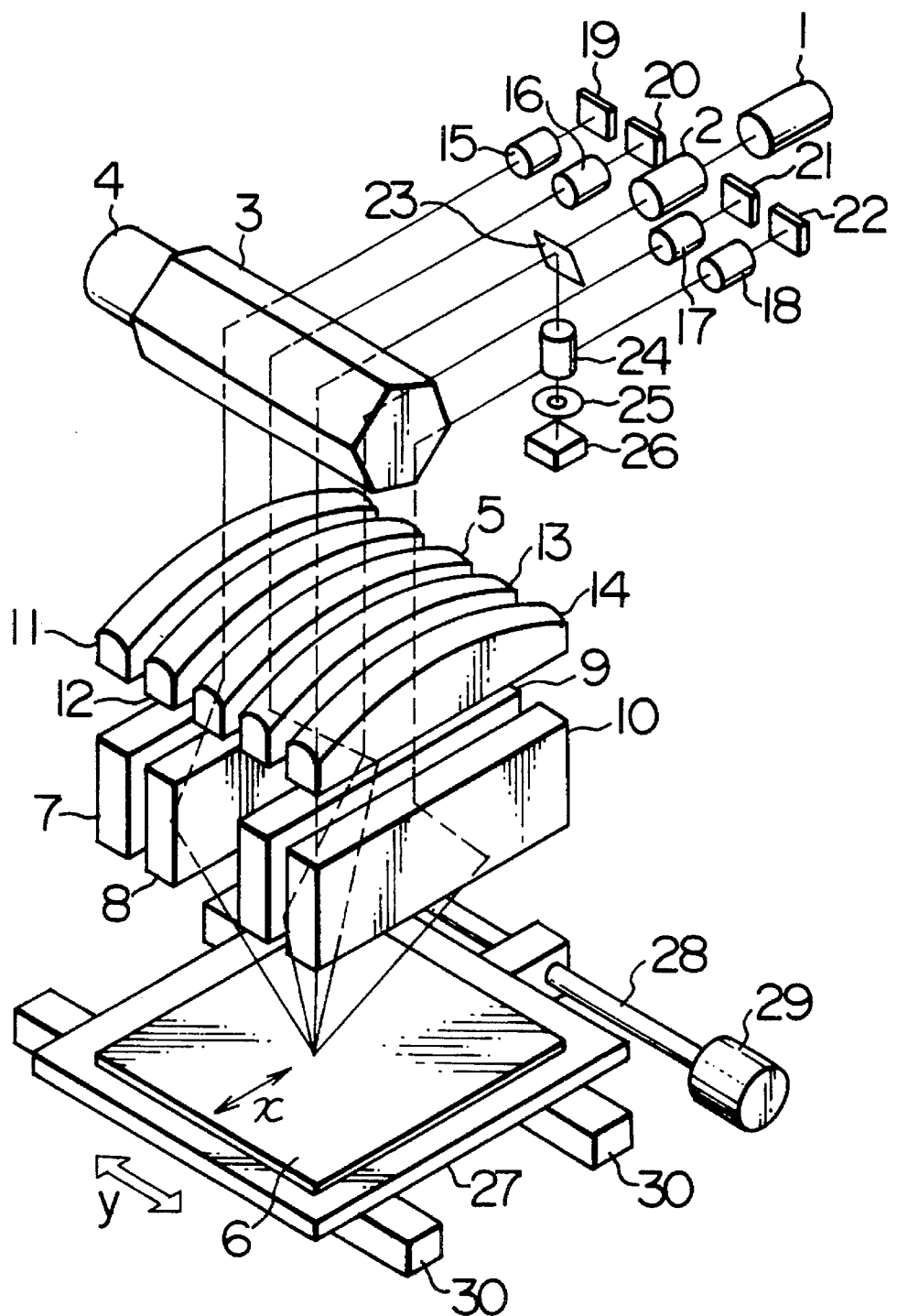
FIG. 1 is a perspective view of an embodiment of a packaged printed circuit board inspection apparatus according to the present invention.

Embodiments of the present invention will now be described with reference to the accompanying drawings. FIG. 1 shows an embodiment of an apparatus for inspection of packaged printed circuit boards according to the invention. Referring to FIG. 1, a light source 1 generates a fine light beam to be irradiated on a packaged printed circuit board 6, a collimator lens system 2 collects the fine light beam from the light source 1 into a parallel flux of light, a polygon mirror 3 deflects the parallel light flux and deflects reflection beams from the packaged printed circuit board 6, a polygon motor 4 drives the polygon mirror 3 to rotate the same, and a light projection fθ lens 5 collects the parallel light flux deflected by the polygon mirror 3 and irradiates it onto the packaged printed circuit board 6 substantially vertically thereto. The packaged printed circuit board 6 is an object to be inspected.

Optical path correcting optical systems 7, 8, 9 and 10 receive beams reflected in four directions from an irradiation position of the fine light beam on the packaged printed circuit board and correct optical paths of the reflection beams in order to guide the reflection beams to light receiving fθ lenses 11, 12, 13 and 14, respectively. The light receiving fθ lenses 11, 12, 13 and 14 are adapted to guide the reflection beams passing through the optical path correcting optical systems 7, 8, 9 and 10 to the polygon mirror 3. Lenses 15, 16, 17 and 18 for semiconductor position sensing devices (PSD) collect the reflection beams passing through the light receiving fθ lenses 11, 12, 13 and 14 and deflected by the polygon mirror 3. PSD's 19, 20, 21 and 22 receive the reflected beams collected by the lenses 15, 16, 17 and 18 for PSD's and produce electrical outputs which comply with receiving positions.

Of the reflection beams from the irradiation position of the fine light beam on the packaged printed circuit board 6, only a beam reflected vertically to the packaged printed circuit board 6 and returning along the light projection optical axis through the light projection fθ lens 5 and polygon mirror 3 is deflected by a tunnel mirror 23. A lens 24 collects the reflection beam deflected by the tunnel mirror 23. An aperture 25 blocks reflection beams reflected in other directions than the vertical direction. A photodiode 26 receives the reflection beam in the vertical direction and converts a receiving light quantity into an electrical output.

A table 27 is adapted to fix the packaged printed circuit board. A ball screw 28 is rotated to move the table 27 in a subsidiary scanning direction (direction of arrow y). The ball screw 28 is rotated by a ball screw motor 29 and the table 27 is guided on guide rails 30, 30. The operation of the packaged printed circuit board inspection apparatus having the above construction will now be described.

A fine light beam generated from the light source 1 is converted into a parallel flux of light by the collimator lens system 2, and the parallel light flux passes through a hole of the tunnel mirror 23, is deflected by the polygon mirror 3 and is collected by the light projection fθ lens 5 into a fine light beam on the fine light beam irradiation optical axis. This fine light beam on the fine light beam irradiation optical axis is irradiated on the packaged printed circuit board 6 substantially vertically thereto. At that time, in accordance with the rotation of the polygon mirror 3 driven for rotation by the polygon motor 4, the fine light beam emitted from the light source 1 is scanned on, the packaged printed circuit board 6 in a main scanning direction (direction of arrow x) shown in the Figure. Reflection beams scattered from a scanning position on the packaged printed circuit board 6 are guided to the light receiving fθ lenses 11, 12, 13 and 14 by means of the optical path correcting optical systems 7, 8, 9 and 10.

Of the reflection beams scattered from an irradiation position on the packaged printed circuit board 6, reflection beams each having an angle between the fine light beam irradiation optical axis and its reflection beam optical axis (hereinafter called a nodding angle) which is substantially constant regardless of the change of scanning position of the fine light beam and an angle between a projection component of the reflection optical axis on a plane vertical to the fine light beam irradiation optical axis and the scanning direction (hereinafter called an allotting angle) which is also substantially constant regardless of the change of scanning position of the fine light beam, that is, reflection beams each having a directional vector which is substantially constant regardless of the change of scanning position of the fine light beam, are received by the optical path correcting optical systems 7, 8, 9 and 10. Then, the received reflection beams are caused to be incident on the light receiving fθ lenses 11, 12, 13 and 14 at positions which are substantially coincident with the fine light beam irradiation optical axis in the main scanning direction (direction of arrow x) regardless of the change of scanning position.

As an example of each of the optical path correcting optical systems 7, 8, 9 and 10, a system using mirrors and prisms as exemplified in FIGS. 2A and 2B may be considered. Taking the optical path correcting optical system 9 as a representative, FIG. 2A schematically shows the optical path correcting optical system 9 as viewed in the main scanning direction (x direction) and FIG. 2B schematically shows the optical path correcting optical system 9 as viewed in the subsidiary scanning direction (y direction). The construction and operation of this system will be described hereunder.

A reflection beam from the packaged printed circuit board 6 is deflected by a mirror 31 to a direction which is substantially vertical to the subsidiary scanning direction so as to be incident on a prism 33. At that time, the prism 33 deflects the reflection beam in such a manner that even when the scanning position changes from, for example, b to c within an entire range a to d of scanning width in the main scanning direction, a distance dx between b and c in the main scanning direction substantially equals a distance dx1 between b1 and c1. Since the reflection beam having passed through the prism 33 is not vertical to the main scanning direction, it is deflected so as to be substantially vertical to the main scanning direction and displaced in the main scanning direction so as to impinge on the light receiving fθ lens 13 substantially vertically thereto at a position substantially coincident with the fine light beam irradiation optical axis in the main scanning direction.

In this case, since the optical path length extending from the fine light beam irradiation position to the incident position on the light receiving fθ lens 13 differs depending on the scanning position, reflection beams in the optical axis direction will be collected on different positions. Consequently, the size of an image of a reflection beam received by a PSD will differ depending on the scanning position and inaccurate measurement will sometimes be conducted. To cope with this problem, it is preferable that the prism 33 deflect reflection beams within the entire range a to d of scanning width such that, for example, an optical path extending to b2 on the light receiving fθ lens 13 when the scanning position is at b substantially equals an optical path extending to c2 on the light receiving fθ lens 13 when the scanning position is at c.

Cylindrical lenses 32 and 36 are lenses for collecting a reflection beam scattered in the subsidiary scanning direction in order to increase the light quantity of the reflection beam received by the PSD 21. When the height of an object to be measured changes, the incident position in the subsidiary scanning direction on the light receiving fθ lens 13 changes with that height. But in the present embodiment, focal lengths of the cylindrical lenses are adjusted, so that the reflection beam having passed through the light receiving fθ lens 13 can always be substantially vertical to the subsidiary scanning direction regardless of a change in the height. However, in an alternative method, focal lengths of the cylindrical lenses may be adjusted such that the reflection beam can always be incident on the light receiving fθ lens substantially vertically thereto even when the height changes. Any one of the two methods may be selected which can optimize an optical collecting state on the PSD and a change state of light receiving position on the PSD due to a change in the height.

FIG. 3 shows another example of the construction of the optical path correcting optical system. Mirror 31, prism 33 and mirrors 34 and 35 have the same functions as those in the foregoing construction. In the construction of FIGS. 2A and 2B, however, mutually parallel arrangement of the mirrors 34 and 35 is difficult to achieve and as a result the incident position in the subsidiary scanning direction on the light receiving fθ lens differs depending on the change of the scanning position. Therefore, in order that the incident position in the subsidiary scanning direction on the light receiving fθ lens can remain unchanged even when the scanning position changes, cylindrical lenses 32 and 36 are rotated about the optical axis.

A concrete method of rotating the cylindrical lenses 32 and 36 will be described below. The cylindrical lens 32 is rotated about an optical axis (A) so that, even when the scanning position changes, the incident position a reflection beam on the cylindrical lens 36 may not be displaced in the subsidiary scanning direction under the condition that the cylindrical lens 36 is not rotated. Under this condition, however, the reflection beam incident on the cylindrical lens 36 is not vertical to the subsidiary scanning direction and so the reflection beam does not impinge on the light receiving lens fθ vertically thereto. Accordingly, the cylindrical lens 36 is rotated about an optical axis (B) so that the reflection beam may impinge on the light receiving fθ lens substantially vertically thereto. By rotating the cylindrical lenses 32 and 36 in the manner as above, the incident position on the light receiving fθ lens can remain unchanged in the subsidiary scanning direction even when the scanning position changes.

Figure 4:
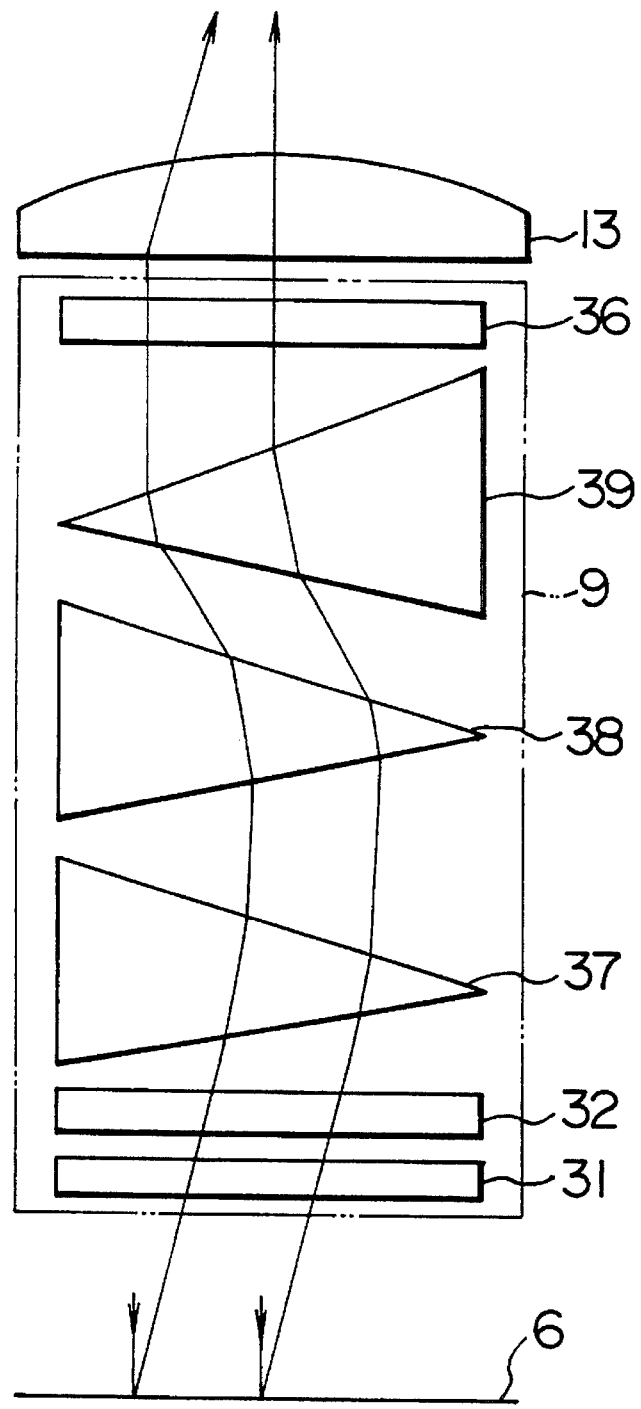
FIG. 4 is a diagram showing the construction of still another optical path correcting optical system of the apparatus.

FIG. 4 illustrates still another example of the construction of the optical path correcting optical system, schematically showing an optical path correcting optical system 9 as viewed in the subsidiary scanning direction. Three prisms 37, 38 and 39 are used in combination to attain a function similar to that of the optical path correcting optical system of FIGS. 2A and 2B. In this case, the two mirrors in pair are not used and therefore any displacement in the subsidiary scanning direction due to a change in the scanning position does not occur, thus eliminating the necessity of the rotation of cylindrical lenses about the optical axes.

In the foregoing constructions of FIGS. 2A, 2B, 3 and 4, the light projection fθ lens and light receiving fθ lenses are formed separately, but the light projection fθ lens 5 and light receiving fθ lenses 11, 12, 13 and 14 can be unified to form a single fθ lens. Through the unification, the production cost of the fθ lens can be decreased, and adjustments of the light projection and receiving fθ lenses after assembly are not required to be carried out separately but can be effected simultaneously in a simplified manner. Further, the light projection fθ lens or the light receiving fθ lens may takes the form of a cylindrical fθ lens which has a curvature in only the scanning direction. In this case, the four light receiving fθ lenses can be produced at a time and the production cost can be decreased.

By virtue of the above construction of the optical path correcting optical system 9, only a reflection beam having a directional vector which is constant regardless of the change of the scanning position can be incident on the light receiving fθ lens 13 at a position substantially coincident with the fine light beam irradiation optical axis in the scanning direction. Since the light receiving fθ lens 13 and the light projection fθ lens 5 has the same shape, the reflection beam is guided to the polygon mirror 3 by way of the same route as the projected fine light beam. The reflection beam is then deflected by the polygon mirror 3 to form an image of the reflection beam at a position on the PSD 21 which complies with a height of the fine light beam irradiation position on the printed circuit board 6 regardless of the change of the scanning position of the fine light beam. This holds true for the other optical path correcting optical systems 7, 8 and 10 and reflection beams received by the optical path correcting optical systems 7, 8 and 10, respectively, pass through the light receiving fθ lenses 11, 12 and 14 and the lenses 15, 16 and 18 for PSD's and are guided to the PSD's 19, 20 and 22.

Since images of the reflection beams from the packaged printed circuit board 6 are formed on the PSD's at positions complying with a height of the fine light beam irradiation position, the height of the fine light beam irradiation position can be determined by using electrical outputs delivered out of the PSD's at that time. By applying a processing such as selection to be described later to data measured by the PSD's 19, 20, 21 and 22 arranged in four directions, a correct height can be measured regardless of a surface state of the object to be measured.

A reflection beam reflected at the fine light beam irradiation position in the direction of the fine light beam irradiation optical axis (substantially vertical direction) is guided to the photodiode 26 through the light projection fθ lens 5, polygon mirror 3, tunnel mirror 23, lens 24 and aperture 25. In this operation, the reflection beam in the vertical direction is collected by the light projection fθ lens 5 and lens 24 and the thus collected reflection beam is received by the photodiode 26. Beams other than the reflection beam in the fine light beam irradiation optical axis direction are blocked by the aperture 25 interposed between lens 24 and photodiode 26. Accordingly, only the light quantity of the reflection beam reflected at the fine light beam irradiation position in the fine light beam irradiation optical axis direction can be measured correctly.

According to the present embodiment, four pieces of brightness data and four pieces of height data can be acquired in four directions for a single measuring point by means of the four PSD's 19, 20, 21 and 22. Available as a method for selection processing of the four brightness data pieces is a method of determining the maximum value of the four data pieces. Available as a method for selection processing of the height data pieces is, for example, a method in which data pieces unwarrantable of measurement accuracy are removed and the remaining data pieces are averaged or a method, suitable for the case of the number of the remaining data pieces being large, in which data pieces of the maximum and minimum levels are removed and the remaining data pieces are averaged. The photodiode 26 receiving the reflection beam vertically reflected from the packaged printed circuit board 6 delivers a large output when the inclination of a soldering surface is small or soldering is missed and the quantity of reflection beam in the vertical direction becomes large but conversely, it delivers a small output when the inclination of a soldering surface is large and the quantity of reflection beam becomes small. Therefore, when the outputs of the PSD's are too small to measure the height of a soldering surface correctly, the brightness information from the photodiode 26 can be referred to.

Thus, the quality of a packaging state of the packaged printed circuit board can be inspected by comparing the height information and brightness information which have been passed through the selection processings with height information and brightness information which have precedently been obtained from a criterion of packaged printed circuit board.

Figure 5:
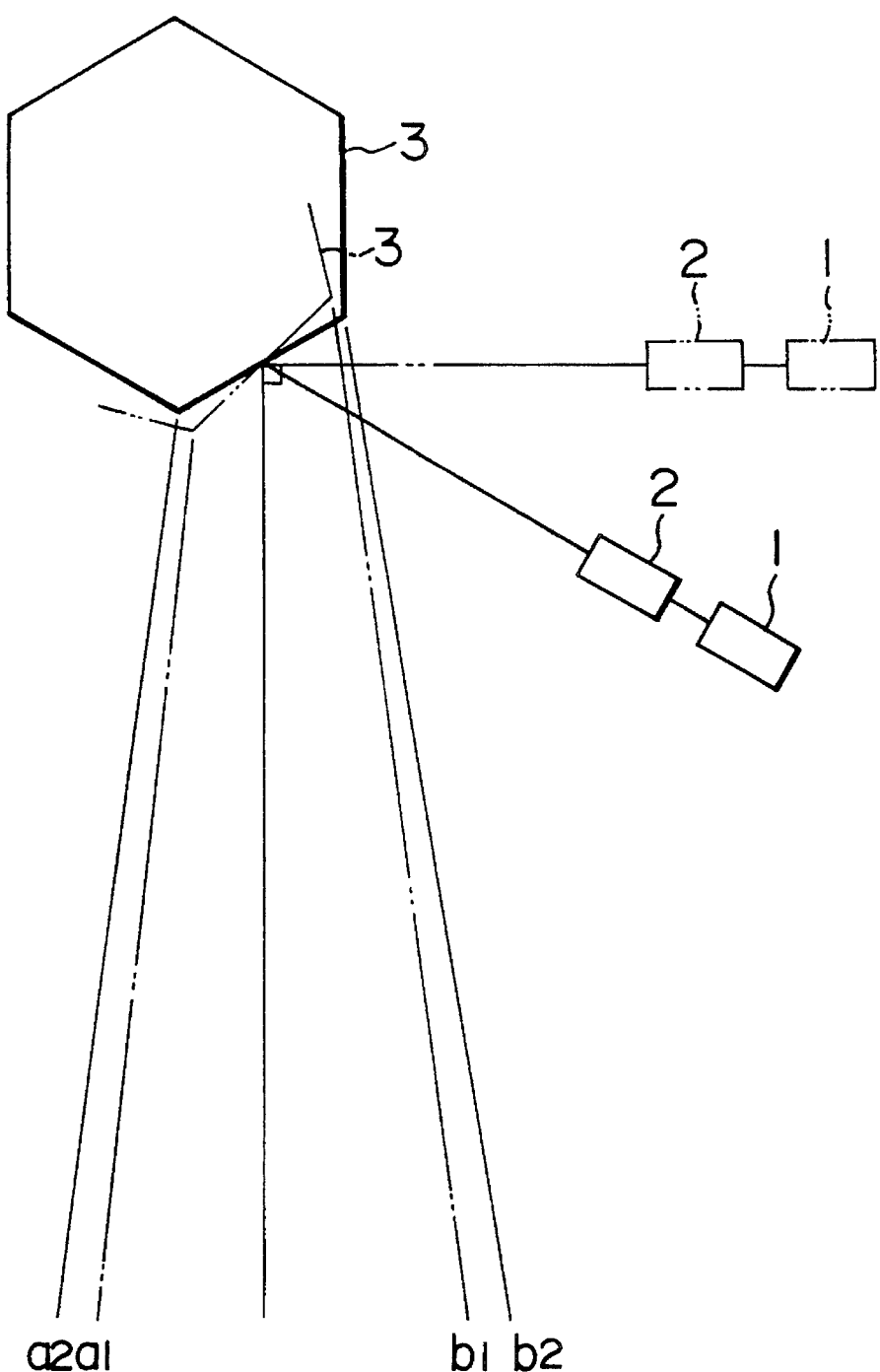
FIGS. 5 to 7 are diagrams useful to explain a light projection unit of the apparatus.

FIG. 5 shows the light receiving range available when a reflection beam of an irradiated fine light beam emitted from the light source 1 and passed through the collimator lens system 2 is passed through the light receiving fθ lens and deflected by the polygon mirror 3. A light receiving range available when the light source 1 is arranged such that the optical axis of the fine light beam emitted from the light source 1 and reaching the polygon mirror 3 makes an angle of 90° to the perpendicular of the packaged printed circuit board 6 is depicted by dotted line and a light receiving range available for an arrangement in which the angle is 60° is depicted by solid line.

When the angle is 90°, the polygon mirror is allowed to receive reflection beams from a range extending from a1 to b1 in the scanning direction and the quantities of the reflection beams from the range of from a1 to b1 are sometimes insufficient to satisfy the performance of the PSD. When the angle is smaller than 90°, amounting to 60°, larger quantities of reflection beams from a range extending from a2 to b2 in the scanning direction can be received as compared to the case of 90° and a quantity of light which can satisfy the performance of the PSD can be insured. The advantage of the acute-angle arrangement of the light projection optical axis holds true for all reflection angles within the scanning range (−θ to +θ).

Figure 6:
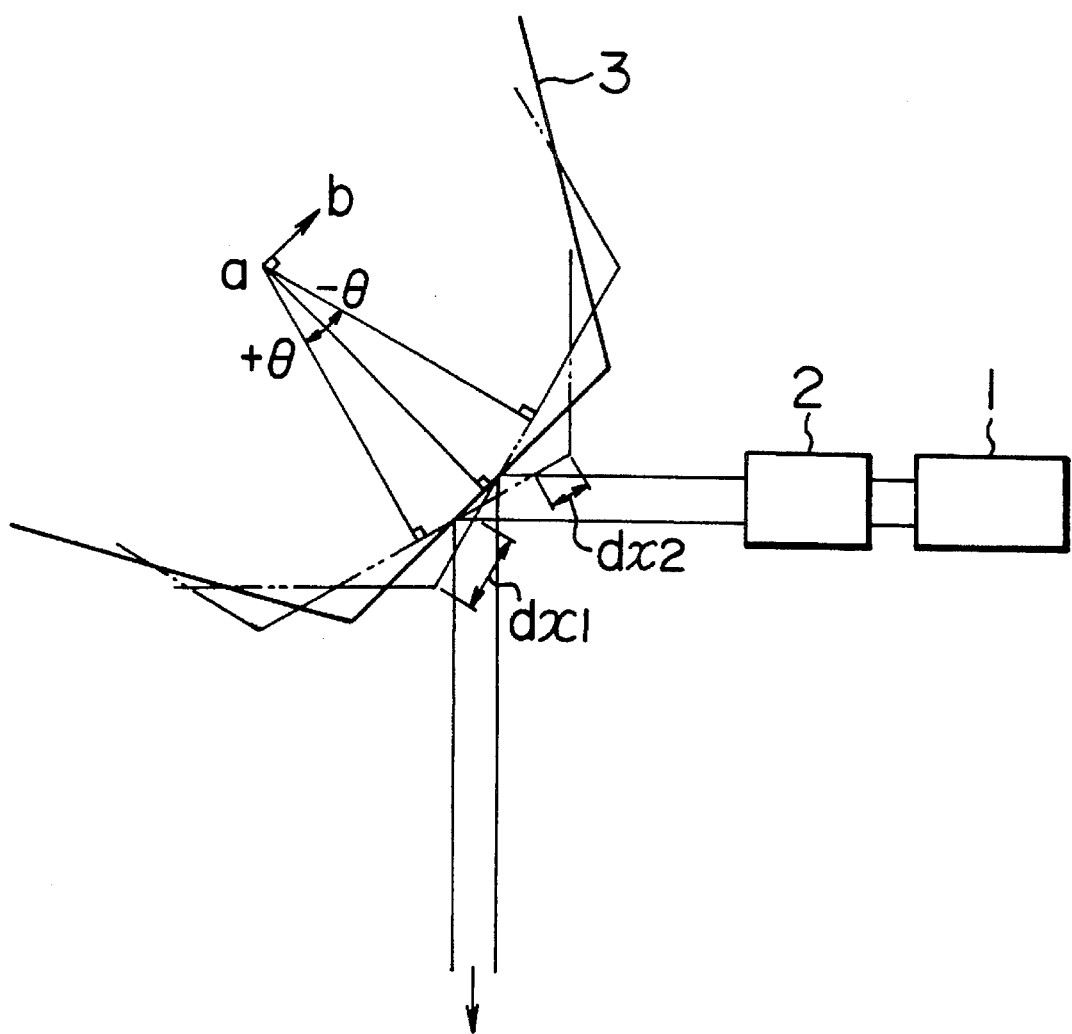

FIG. 6 shows an arrangement in which the position of the rotary shaft of the polygon mirror 3 in the above embodiment is displaced. In order to permit the parallel light flux having passed through the collimator lens system 2 to uniformly impinge upon the reflection surface of the polygon mirror regardless of the rotation angle of the polygon mirror 3, the rotary shaft of the polygon mirror is offset. More specifically, the rotary shaft of the polygon mirror is offset from a to b so that a reflection area dx1 when the rotation angle of the polygon mirror is −θ may equal a reflection area dx2 when the rotation angle is +θ. Uniform impingement of the parallel light flux upon the reflection surface can afford to ensure the effective use of the reflection surface and prevent the reflection surface of the polygon mirror from being burnt out.

With the rotary shaft of the polygon mirror offset, the receiving light quantity of the reflection beam in the direction vertical to the packaged printed circuit board differs in the scanning direction for the rotation angle of the polygon mirror being −θ and the rotation angle being +θ, indicating that the light quantity is less for −θ. The performance of the photodiode will fail to fulfill itself sufficiently with the less light quantity.

Figure 7:
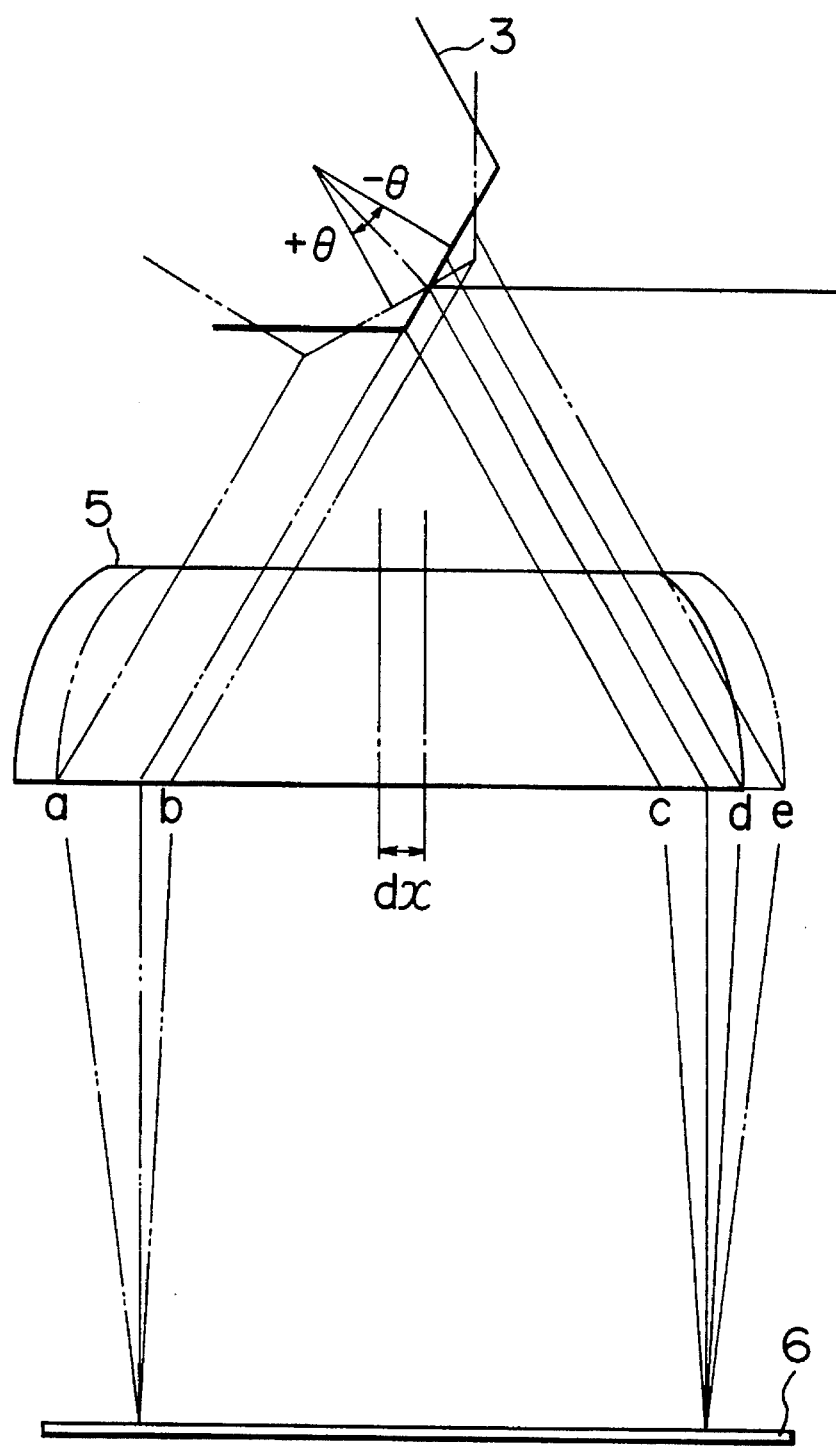

Accordingly, as shown in FIG. 7, the light projection fθ lens is offset in parallel to the main scanning direction (x direction) to ensure that the light quantity for −θ is increased to cancel the difference between the receiving light quantities for the rotation angles of ±θ.

More particularly, when the rotation angle is +θ, reflection beams can be received by the entire reflection surface of the polygon mirror. In other words, reflection beams from a range of from a to b can be received. However, with the light projection fθ lens 5 not offset, some of reflection beams from an edge portion of the light projection fθ lens are cut when the rotation angle is −θ, with the result that only reflection beams from a range of from c to d can be received and the receiving light quantity is less for the rotation angle being −θ. To cope with this problem, the symmetrical axis of the light projection fθ lens is offset by dx in the scanning direction so that reflection beams from a range of from c to e can be received.

For the same reason, the difference between receiving light quantities for the rotation angles of ±θ of the polygon mirror can be cancelled for reflection beams having passed through the light receiving fθ lenses 11, 12, 13 and 14 by offsetting the light receiving fθ lenses.

Figure 8:
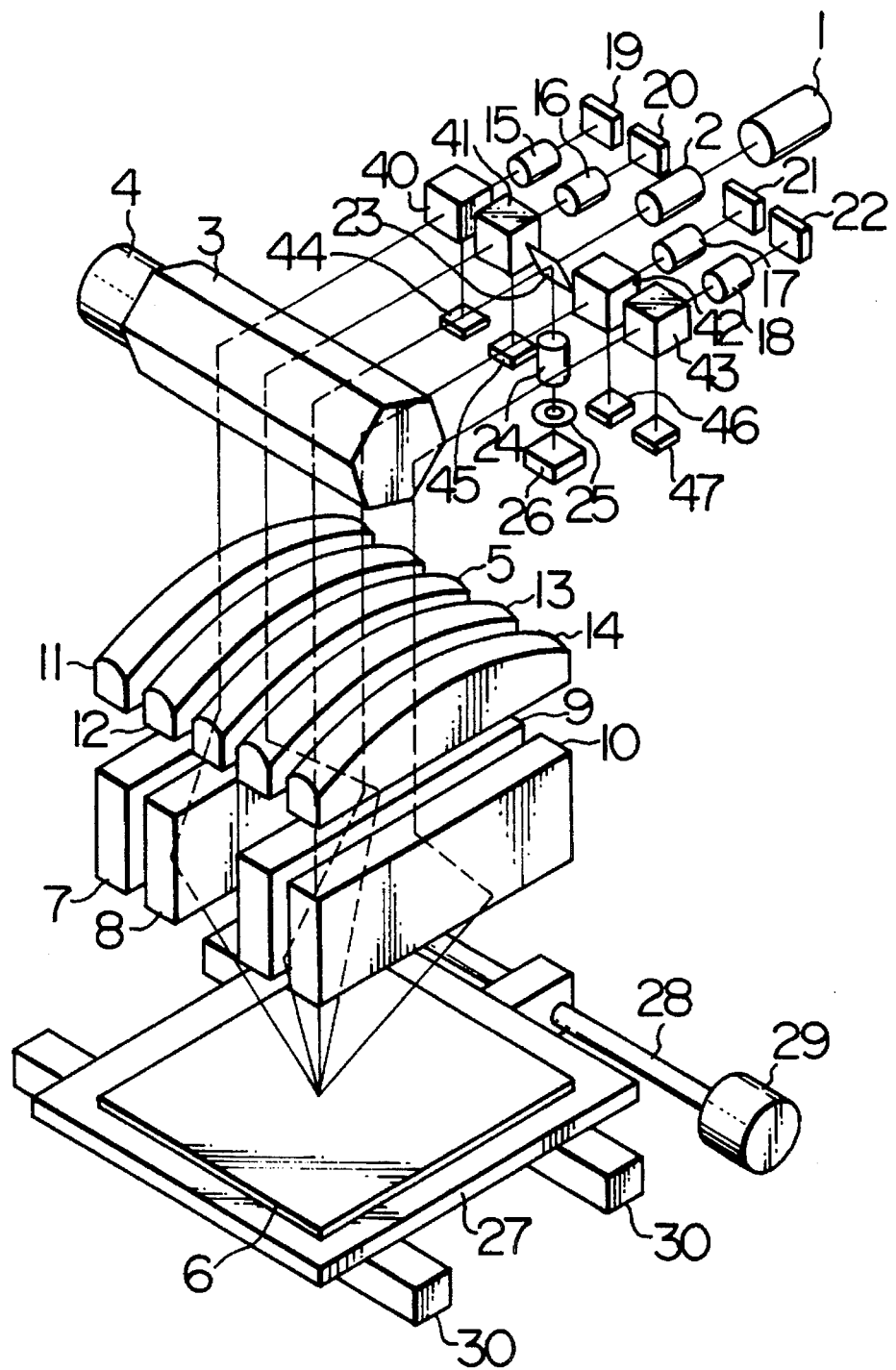
FIGS. 8 and 9 are diagrams for explaining another embodiment of the light receiving unit of the apparatus.

FIG. 8 schematically shows a light receiving unit in the above embodiment. This construction is different from the FIG. 1 construction in that AO devices (acousto-optical devices) 40, 41, 42 and 43 and scanning position correcting circuits 44, 45, 46 and 47 for receiving scanning position signals indicative of a scanning position in the main scanning direction on the packaged printed circuit board and delivering scanning position correcting signals to the AO devices are provided on optical paths between the polygon mirror 3 and the respective lenses 15, 16, 17 and 18 for PSD's, whereby optical paths of reflection beams are corrected.

Figure 9:
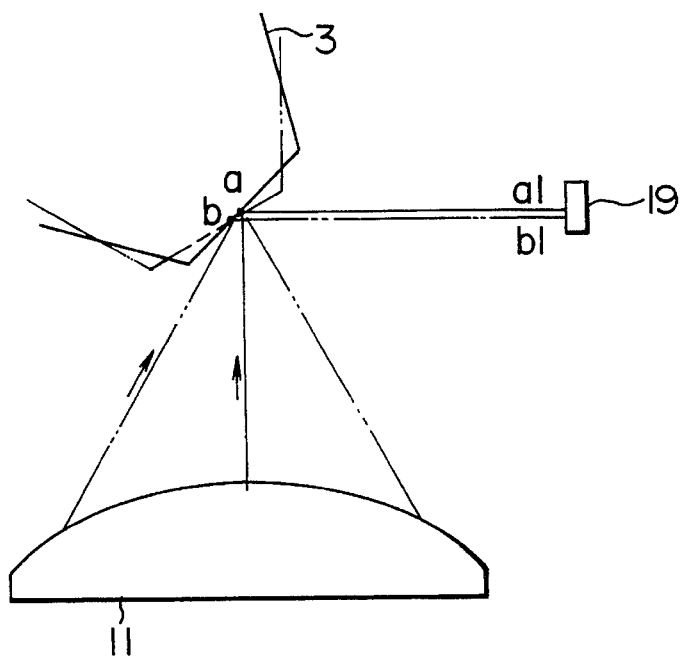

The reason why optical paths of reflection beams are corrected will be described with reference to FIG. 9. As the polygon mirror rotates, the reflection position shifts from a to b. Consequently, even when the same height is scanned, the light receiving position of the PSD 19 shifts from a1 to b1 in accordance with the scanning position. Further, the performance is different for individual optical path converting units provided for four directions because of error and accuracy of assembly of the optical path converting units and as a result, light receiving positions in the scanning direction of the PSD's are different for the individual optical path converting units. Because of the movement of the PSD light receiving position, a PSD having a size corresponding to an amount of movement must be used, giving rise to an increase in light receiving area of the PSD. As the light receiving area of the PSD increases, the frequency characteristics are deteriorated, and the performance differs for a central portion and both side portions of the PSD and must be corrected.

Figure 10:
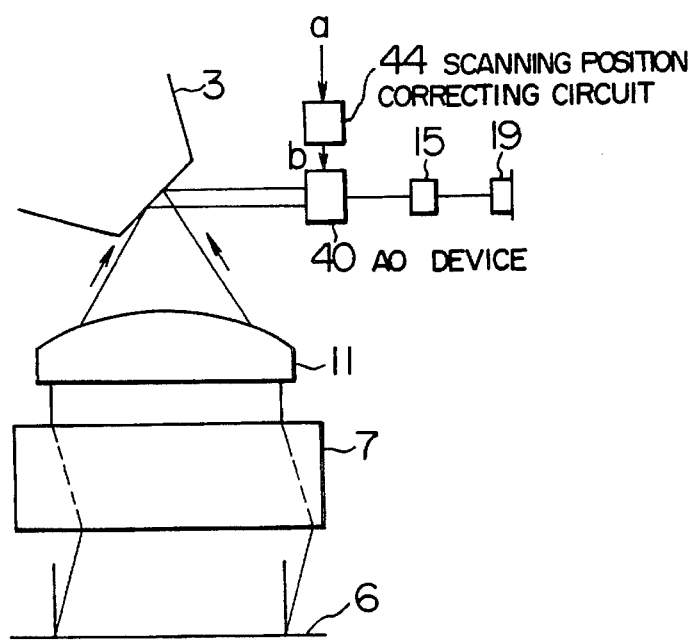
FIG. 10 is a diagram for explaining still another embodiment of the light receiving unit of the apparatus.

In the light of the above, means for correcting the optical path of the reflection beam deflected by the polygon mirror in accordance with the scanning position is provided in each of the optical paths of reflection beams in the four directions. This means corresponds to the AO device. As shown in FIG. 10, when receiving a scanning position signal a indicative of the present scanning position in the main scanning direction (x direction), the scanning position correcting circuit 44 delivers a scanning position correcting signal b to the AO device 40. Responsive to this signal, the AO device 40 corrects the optical path of the reflection beam such that the light receiving position in the scanning direction remains unchanged even when the scanning position changes.

As described above, the AO devices are provided in the packaged printed circuit board inspection apparatus of FIG. 1 to correct the optical path such that the PSD can always receive the reflection beam at the same position regardless of the scanning position, thereby improving the performance of the PSD.

In place of the AO devices, PSD light receiving portion drive units 48, 49, 50 and 51 for moving the lenses 15, 16, 17 and 18 for PSD's and the PSD's 19, 20, 21 and 22 in accordance with the scanning position may be provided as shown in FIG. 11 in order that the light receiving portion of the PSD can be moved to allow the PSD to take the same light receiving position regardless of the change of the scanning position.

Figure 12:
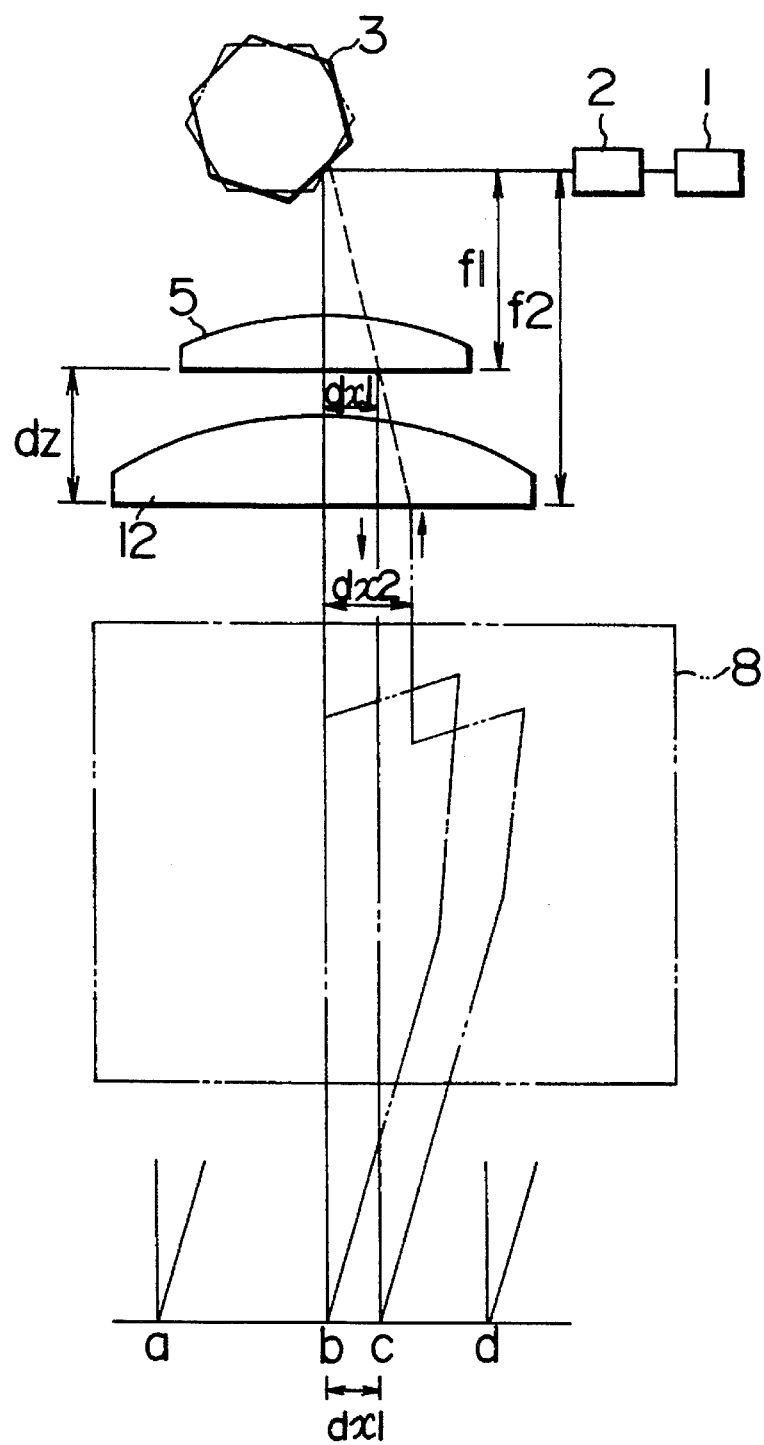
FIG. 12 is a diagram showing the construction of another embodiment of the light projection and light receiving system of the apparatus.

FIG. 12 is a diagram as viewed in the subsidiary scanning direction of the packaged printed circuit board inspection apparatus, showing a configuration in which the focal length of a light projection fθ lens differs from that of a light receiving fθ lens. For the sake of using fθ lenses of different focal lengths in light projection and light reception, an angle at which the fine light beam is incident on the light projection fθ lens must be equal to an angle at which the reflection beam goes out of the light receiving fθ lens. In other words, the following equation must be satisfied.

$$f1/dx1 = f2/dx2$$

where f1: focal length of light projection fθ lens
f2: focal length of light receiving fθ lens
dx1: scanning distance of light projection
dx2: distance corresponding to dx1 on the backside of optical path converting unit.

Accordingly, a prism which deflects the reflection beam in compliance with $$dx2 = f2/f1 * dx1$$

is used in the optical path converting unit. The position in z direction of the light receiving fθ lens is moved by dz so that the reflection beam may be allowed to be incident on the polygon mirror. With this construction, the size of the light projection fθ lens 5 can be smaller than that of the light receiving fθ lens 12 and the cost can be reduced.

While in the present embodiment the reflection beams are measured in the four directions as described above, reflection beams may be measured in more than four directions by increasing the number of the optical path correcting optical systems, light receiving fθ lenses, lenses for PSD's and PSD's used in the present embodiment. In the present embodiment, with a view of preventing the characteristics of trigonometrical survey from being changed depending on the scanning position, only a reflection beam having a constant directional vector regardless of the change of the scanning position is taken out and its optical path is corrected but alternatively, only a reflection beam making a constant angle to the fine light beam irradiation optical axis (constant nodding angle) may be taken out and its light path may be corrected. Further, the tunnel mirror used in the present embodiment may be replaced with a half mirror.

The elongated polygon mirror which is long in the direction of rotary shaft is used in the present embodiment. By increasing the length of the polygon mirror, a margin of arrangement of the optical path correcting optical systems can be gained, thus ensuring that the number of the optical path correcting optical systems can be increased to permit measurement of reflection beams in more than four directions. Further, since the length of individual optical parts of the optical path converting unit can be increased in the subsidiary scanning direction (longitudinal direction of the polygon mirror), the light quantity of a reflection beam can be increased in the subsidiary scanning direction and consequently the receiving light quantity of the PSD can be increased to raise inspection accuracy.

The rotary shaft of the polygon mirror is not vertical to the printed circuit board (parallel to the direction of gravity) but is parallel to the printed circuit board (vertical to gravity). A rotary shaft laid vertically to the printed circuit board is effective to decrease a deflection to the rotary shaft. But, the elongated polygon mirror laid in parallel to the printed circuit board in the present embodiment has its rotary shaft journalled at opposite ends and therefore a deflection of the rotary shaft can be suppressed to a minimum; and in addition, the number of mirrors for deflecting the fine light beam to irradiate it onto the printed circuit board can be small and the structure of the optical components can be compact.

Incidentally, in the packaged printed circuit board inspection apparatus of the above construction, the photodiode 26 plays the role of detecting, on the basis of a receiving light quantity, whether a soldering surface is inclined or planar. With the unitary photodiode 26, however, only a decision as to whether the soldering surface is inclined or planar is permitted but a decision as to a direction in which the soldering surface is inclined is not possible. Accordingly, in the packaged printed circuit board inspection apparatus according to the present embodiment, a four-division photodiode is used as the photodiode 26. With the four-division photodiode used, an output of one of four divisions which lies in a direction in which the soldering surface is inclined is maximized and hence an inclination direction of the soldering surface can be determined.

This will be described in greater detail with reference to FIG. 13. FIG. 13 is useful to explain the construction using a four-division photodiode, showing a four-division photodiode 52, a soldering surface of the packaged printed circuit board, and a lead tip 54. For simplicity, the light projection fθ lens, polygon mirror, tunnel mirror, lens and aperture are omitted. A principal ray of a reflection beam is indicated by an arrow-headed solid line and a peripheral ray of the reflection beam is indicated by dotted line. The four-division photodiode 52 receives the peripheral ray indicated by dotted line. When the soldering surface is inclined, the principal ray of the reflection beam is not directed to a direction of fine light beam irradiation optical axis A but is inclined to a direction in which the inclined soldering surface is inclined as shown in FIG. 13. Since the quantity of light of the peripheral ray decreases in proportion to the distance from the principal ray, the four-division photodiode receiving the peripheral ray has a maximum receiving light quantity at a division lying in the direction in which the soldering surface is inclined. In FIG. 13, the receiving light quantity becomes maximum at a division 3. In other words, by detecting receiving light quantities at divisions 1 to 4 and examining a division of the maximum light quantity, a direction in which the soldering surface is inclined can be found. By applying operations to receiving light quantities of the divisions 1 to 4, an inclination angle of the soldering surface can be determined.

The four-division photodiode is exemplified as above but a photodiode having four or more divisions may be used. Alternatively, a plurality of unitary photodiodes may be arranged and receiving light quantities thereof may be detected. In an alternative, a two-dimensional PSD may be used in place of the photodiode to determine a position of the principal ray of reflection beams.

In the packaged printed circuit board inspection apparatus shown in FIG. 1, the light quantity in the subsidiary scanning direction of a reflection beam reflected vertically to the packaged printed circuit board is determined by a width in the subsidiary scanning direction of the light projection fθ lens 5 and when the width in the subsidiary scanning direction of the light projection fθ lens is not allowed to be long, the light quantity received by the photodiode decreases and the inspection accuracy is degraded.

Accordingly, with a view of increasing the receiving light quantity of the reflection beam in the vertical direction, a special cylindrical lens 55 is provided as shown in FIG. 14. In the Figure, the reflection beam reflected vertically to the packaged printed circuit board is indicated by solid line and the projection fine light beam is indicated by dotted line. The special cylindrical lens 55 is a lens having a curvature only in the subsidiary scanning direction and its curved apex is partly cut and flattened. The special cylindrical lens thus provided collects beams in the subsidiary scanning direction of the reflection beam reflected vertically to the packaged printed circuit board to raise the accuracy of the inspection by the photodiode 26.

With this construction, a fine light beam having passed through the light projection fθ lens 5 passes through the special cylindrical lens 55 and is irradiated on the packaged printed circuit board 6 without being affected by the special cylindrical lens 55 because of passage through the flattened portion of the special cylindrical lens. A reflection beam vertical to the packaged printed circuit board 6, on the other hand, passes through the curved portion of the special cylindrical lens 55 and therefore its component beam in the subsidiary scanning direction is collected, thereby securing a light quantity which warrants the inspection accuracy of the photodiode.

In the packaged printed circuit board inspection apparatus in which, of reflection beams of a fine light beam irradiating the packaged printed circuit board vertically thereto, a reflection beam reflected in the substantially vertical direction along the fine light beam optical axis is received to perform inspection of the shape of surface, the above constructions of FIGS. 13 and 14 are advantageous in that an inclination direction of a soldering surface can be detected by receiving a reflection beam in the vertical direction through the use of the photoelectric conversion device having divisions which deliver mutually different electrical outputs and the receiving light quantity can be increased by using the cylindrical lens so worked as not to affect the scanning of the fine light beam on the board, so that the inspection accuracy can be raised.

In the inspection apparatus in which a fine light beam emitted from the light source is deflected by means of the polygon mirror to scan the packaged printed circuit board and beams reflected from the board are taken out, deflected by the polygon mirror and guided to the light receiving unit, the jitters of the polygon mirror must be corrected. In the following embodiments of the present invention, the construction of a jitter corrector applied to the packaged printed circuit board inspection apparatus will be described.

FIG. 15 shows the construction of an embodiment of the jitter corrector according to the present invention. In the Figure, a light source 56 for generating a fine light beam is separate from the light source 1 of FIG. 1, a collimator lens system 57 converts the fine light beam emitted from the light source 56 into a parallel light flux, a collecting lens system 58 collects the parallel light flux into a fine light spot, a polygon mirror 3, identical to that shown in FIG. 1, deflects the fine light beam having passed through the collecting lens system 58 to make the collecting position of the fine light beam scan along an arcuate scanning line 59, and a polygon motor 4, identical to that shown in FIG. 1, drives the polygon mirror 3 to rotate it.

A slit 60 is arranged at a position on scanning line 59 on which the fine light beam from the light source 56 impinges before the packaged printed circuit board 6 is scanned with a fine light beam emitted from the light source 1 of FIG. 1. A surface interval time measuring photoelectric device 61 measures the rotating time of one surface of the polygon mirror and its role may be fulfilled by, for example, a photodiode. A slit 65 is arranged on the scanning line 59 to allow the fine light beam in FIG. 1 to correspond to a scanning start position. A scanning start position detecting photoelectric conversion device 66 detects the fine light beam having passed through the slit 65 to detect the scanning start position on the packaged printed circuit board and its role may be fulfilled by, for example, a photodiode. I/V conversion circuits 62 and 67 convert current signals from the photoelectric conversion devices 61 and 66 into voltage signals. Comparators 63 and 68 compare the voltage signals produced from the conversion circuits 62 and 67 with reference voltages 64 and 69, respectively, to convert them into digital signals of "0" or "1". Denoted by 70 is the measuring system as described in the foregoing embodiment.

The jitter corrector for the polygon mirror constructed as above in the packaged printed circuit board inspection apparatus operates as will be described below. A fine light beam generated from the light source 56 is converted by the collimator lens system 57 into a parallel light flux which in turn is collected by the collecting lens system 58 into a fine light spot to be collected on the scanning line 59. The polygon mirror 3 is driven for rotation by the polygon motor 4 and the polygon mirror in rotation deflects the fine light beam having passed through the collecting lens system 58 to scan it on the scanning line 59 in a direction of arrow x.

As the polygon mirror 3 rotates, the fine light beam initially impinges on the surface interval time measuring photoelectric conversion device 61. Then, a current signal delivered out of the surface interval time measuring photoelectric conversion device 61 is converted by the I/V conversion circuit 62 into a voltage signal which in turn is compared with the reference voltage 64 by means of the comparator 63. The comparator 63 delivers a digital signal which is "0" if the voltage signal is smaller than the reference voltage 64 but "1" if larger. This digital signal serves as a surface interval time measuring signal $\underline{b}$ used to measure a time interval between adjacent surfaces of the polygon mirror 3.

Subsequently, the fine light beam impinges on the scanning start position detecting photoelectric conversion device 66. A current signal delivered out of the scanning start position detecting photoelectric conversion device 66 is converted by the I/V conversion circuit 67 into a voltage signal which in turn is compared with the reference voltage 69 by means of the comparator 68. The comparator 68 delivers a digital signal which is "0" if the voltage signal is smaller than the reference voltage 69 but "1" if larger. This digital signal serves as a scanning start signal $\underline{c}$ indicative of the scanning start position.

The polygon motor 4 delivers a z-phase signal $\underline{a}$ indicative of the origin of rotation angle every revolution.

The z-phase signal $\underline{a}$, surface interval time measuring signal $\underline{b}$ and scanning start signal $\underline{c}$ delivered out of the above devices are mutually related as shown in FIGS. 16A–16E. Firstly, one pulse of z-phase signal $\underline{a}$ is delivered each time the polygon mirror makes one revolution. The origin of rotation angle is defined by this signal. As the polygon mirror rotates subsequently, one pulse of surface interval time measuring signal $\underline{b}$ is delivered at each reflection surface, followed by the delivery of a scanning start signal $\underline{c}$. In the present embodiment, the number of surfaces of the polygon mirror is six and therefore, when the polygon mirror makes one revolution, one pulse of z-phase signal $\underline{a}$, six pulses of surface interval time measuring signal $\underline{b}$ and six pulses of scanning start signal are delivered. The surface interval time is divided by sample blocks to be described later and an interval between sample clocks $\underline{d}$ is determined by the sample interval clock number of reference clock $\underline{e}$ to be described later.

A circuit for generating a sample clock signal for measurement by using these signals will now be described with reference to FIG. 17. When one sample clock of the sample clock signal for measurement is generated, the scanning coordinate position is incremented by one and height measurement is commanded. Firstly, the value of a surface number counter 71 indicating a reflection surface of the polygon mirror is set to zero by a z-phase signal $\underline{a}$. Subsequently, when a fine light beam is incident on the surface interval time measuring photoelectric conversion device 61, a surface interval time measuring signal $\underline{b}$ is obtained which is inputted to the surface number counter 71. Each time that one pulse of surface interval time measuring signal b is inputted, the value of the surface number counter 71 added with one. Thus, the surface number counter 71 delivers a surface number of the polygon mirror currently used for scanning.

The surface interval time measuring signal b sets the value of a surface interval time counter 72 to zero. Subsequently, each time that the surface interval time counter 72 receives one pulse of a reference clock e from a reference clock oscillator 73, the value of the surface interval time counter 72 is added with one. When a surface interval time measuring signal b is newly inputted, the number of pulses produced from the reference clock oscillator 73 between the preceding surface interval time measuring signal b and the current surface interval measuring signal b is held by a latch circuit 74 connected to the surface interval time measuring counter 72. In this manner, a reference pulse number (surface interval time pulse number) of the reference clock oscillator 73 occurring between the preceding surface interval time measuring signal and the current surface interval time measuring signal can be obtained.

On the other hand, a surface interval time measuring signal b again resets the surface interval time measuring counter 72 and a similar operation is repeated. Thereafter, the value (the surface interval time pulse number) of the surface interval time measuring counter 72 held in the latch circuit 74 and the value of the surface number counter 71 are inputted, as an address of the polygon mirror 3, to a decoder 75. The decoder 75 has precedently been written with speed patterns corresponding to surface numbers and surface interval times, and the decoder 75 delivers a speed pattern in accordance with the sum of surface number and surface interval time. For example, the speed patterns are determined such that when the surface number is 1 and the surface interval time is of 1001 to 1010 pulses of the reference oscillator, a speed pattern A is set and when the surface number is 1 and the surface interval time is of 1011 to 1020 pulses of the reference oscillator, a speed pattern B is set. Through this, in the decoder 75, the number of output data pieces (speed patterns) can be smaller than the number of input data (the sum of surface number and surface interval time) pieces and therefore the memory size of a sample interval storage ROM 77 can be decreased. If the storage capacity of the sample interval storage ROM 77 is not limitative, then the decoder 75 can be omitted and surface interval times may be inputted directly to the sample interval storage ROM 77.

The surface interval time measuring signal b also resets a sample number counter 76, and each time that a sample clock is inputted, the value of the sample number counter 76 is added with one. Thus, the output of the sample number counter 76 indicates which sample block (coordinate position) on one scanning line the scanning proceeds to. A time interval between time for measuring a certain coordinate position and time for measuring the next coordinate position is precedently recorded on the sample interval storage ROM 77 in respect of individual coordinate positions and when a coordinate number is inputted to the sample interval storage ROM 77, a time up to the next coordinate position is delivered out of the ROM. Here, the coordinate number is represented by the sum of speed pattern number, surface number and sample number, and the time up to measurement of the next coordinate position is represented by the number of clocks of the reference clock (sample interval clock number N). In other words, when the speed pattern number, surface number and sample number are inputted, as an address, to the sample interval storage ROM 77, a sample interval clock number up to the next sample clock is delivered out of the ROM. The sample interval clock number delivered out of the sample interval storage ROM 77 is inputted to a next stage of subtraction counter 78.

The subtraction counter 78 subtracts one from the value of sample interval clock number each time one pulse of the reference clock is inputted from the reference clock oscillator 73 and when a resulting value becomes zero, a sample clock is delivered as a borrow signal to command measurement. The sample clock is then inputted to the sample number counter 76. The operation of the subtraction counter 78 is controlled by a subtraction counter control circuit 79. When receiving a scanning start signal c, the subtraction counter control circuit 79 delivers an operation start signal to the subtraction counter 78 to command it to start operation. An end sample number storage circuit 80 is written with the value of a final sample number on the one scanning line and the value of the sample number counter 76 is compared with the value of the end sample number storage circuit 80 by means of the subtraction counter control circuit 79. When a current sample number coincides with the end sample number, the control circuit 79 delivers an operation end signal to the subtraction counter 78 to stop the operation thereof. Thus, outside the scanning range, the operation of the subtraction counter 78 is stopped to stop the generation of the sample block.

As described above, by providing the jitter corrector in the packaged printed circuit board inspection apparatus of FIG. 1 and generating sample clocks at time intervals complying with a rotation speed of the polygon mirror, accurate height data at scanning coordinate positions can always be acquired without being affected by irregularity in rotation of the polygon mirror.

When the scanning start position detecting photoelectric conversion device 66 is designed to measure both the scanning start position and surface interval time, the surface interval time detecting photoelectric conversion device 61 may be omitted.

Figure 16:
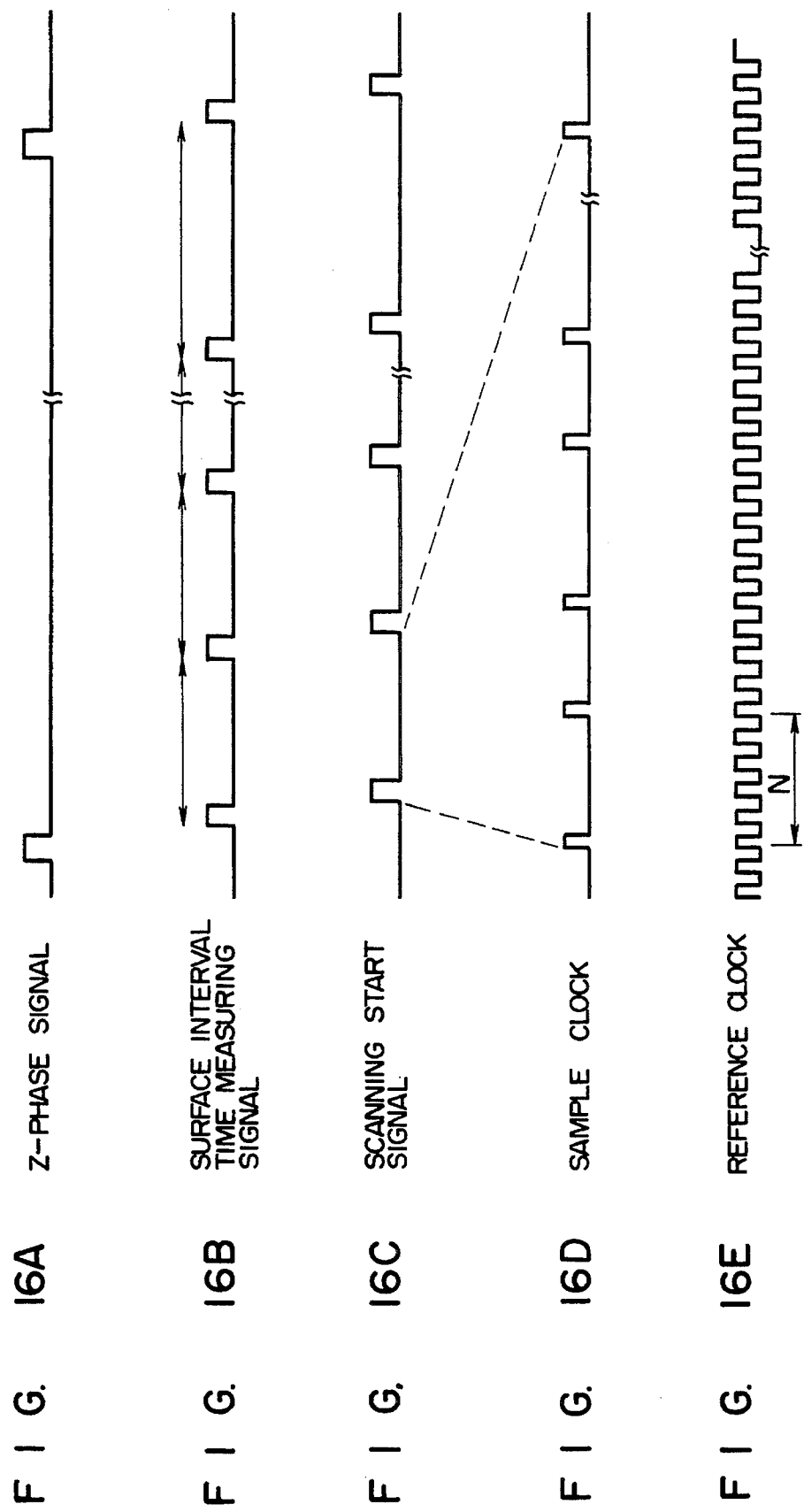
FIGS. 16A to 16E are timing charts for the jitter corrector of FIG. 15.
Figure 17:
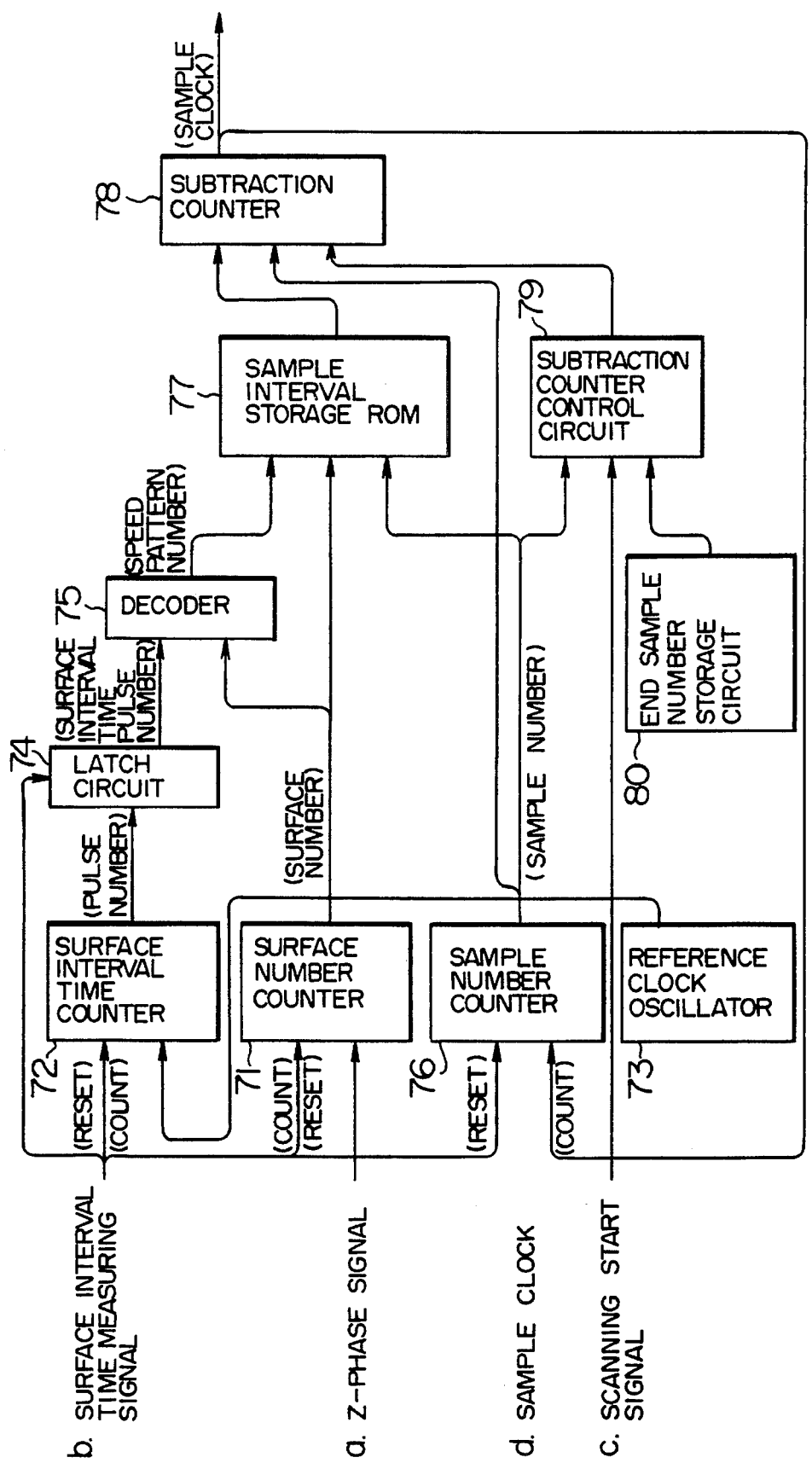
FIG. 17 is a block diagram of the jitter corrector of FIG. 15.

As described above, in the packaged printed circuit board inspection apparatus in which a fine light beam emitted from the first light source is scanned on the packaged printed circuit board by using the polygon mirror and reflection beams from the packaged printed circuit board are deflected by the polygon mirror so as to be guided to the light receiving unit, the jitter corrector as shown in FIGS. 15 to 17 is provided wherein a fine light beam emitted from the second light source separate from the first light source is deflected by the polygon mirror, a rotation speed of the polygon mirror is detected by light receiving means arranged on the scanning line of the fine light beam, and a signal commanding sampling of the surface shape of the board in accordance with the rotation speed is generated.

By generating a sample clock at time intervals complying with the rotation speed of the polygon mirror, accurate height data at scanning coordinate positions can always be acquired without being affected by irregularity in rotation of the polygon mirror.

The construction of another embodiment of the jitter corrector according to the present invention as applied to the packaged printed circuit board inspection apparatus will now be described.

Figure 18:
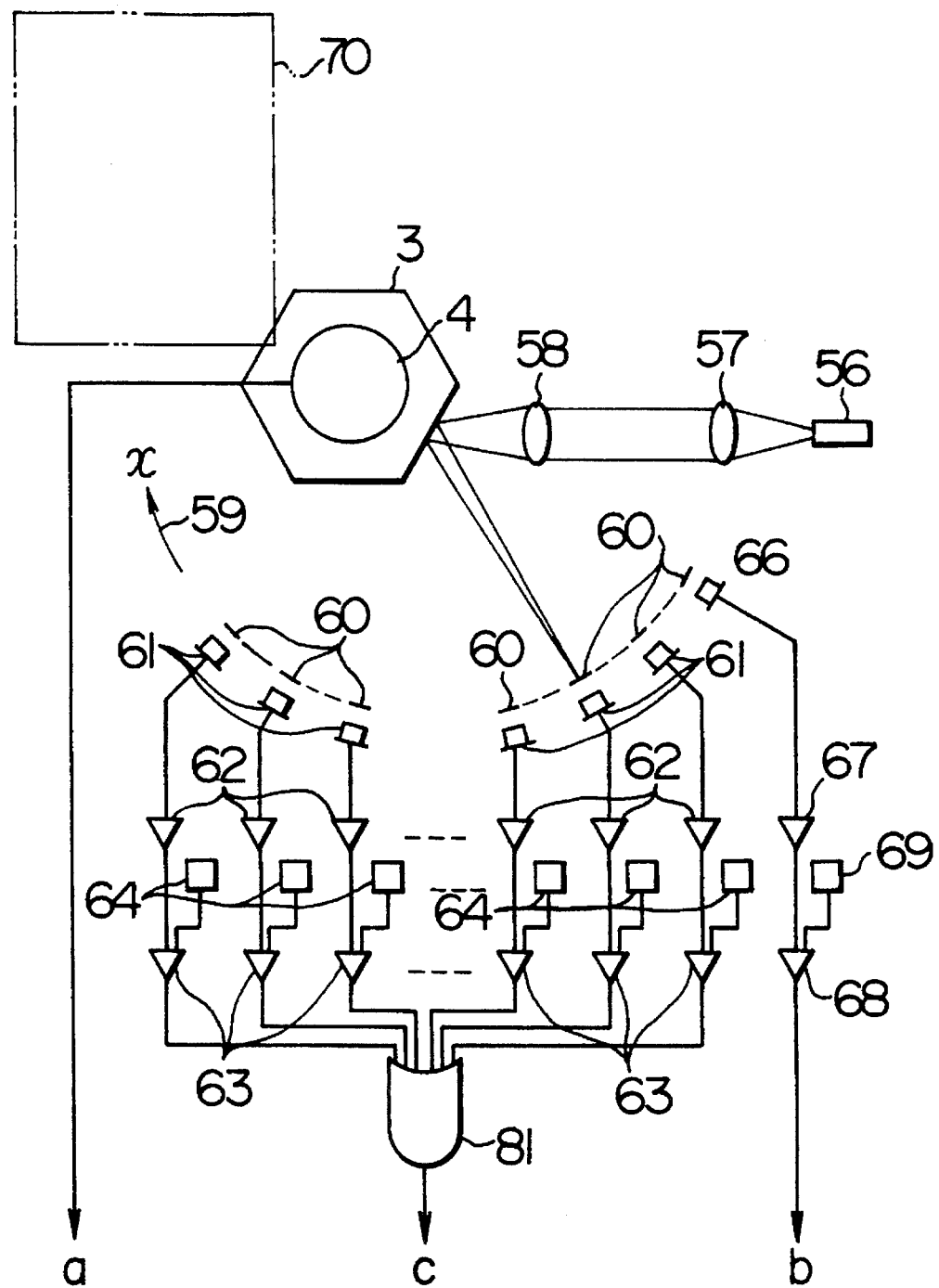
FIG. 18 is a diagram showing the construction of another embodiment of the jitter corrector.

In FIG. 18, a light source 56 for generating a fine light beam is separate from the light source 1 of FIG. 1, a collimator lens system 57 converts the fine light beam emitted from the light source 56 into a parallel light flux, a collecting lens system 58 collects the parallel light flux into a fine light spot, a polygon mirror 3, identical to that shown in FIG. 1, deflects the fine light beam having passed through the collecting lens system 58 to make the fine light beam scan along a scanning line 59 or sweep the scanning line 59, and a polygon motor 4, identical to that shown in FIG. 1, drives the polygon mirror 3 to rotate it.

A slit group corresponds to a scanning range of the packaged printed circuit board and includes slits 60 which are arranged on the arcuate scanning line 59 on which the fine light beam from the light source 56 collects so as to divide the scanning range substantially uniformly. A rotation angle detecting photoelectric conversion device 61 detects the fine light beam having passed through each slit 60 to measure a rotation angle of the polygon mirror 3 and its role may be fulfilled by, for example, a photodiode.

An I/V conversion circuit 62 converts a current signal from each rotation angle detecting photoelectric conversion device 61 into a voltage signal, a comparator 63 compares the voltage signal produced from the I/V conversion circuit 62 with a reference voltage 64 to convert it into a digital signal of "0" or "1". An OR circuit 81 ORs digital signals from the respective comparators 63 to deliver a rotation angle signal.

A scanning start position detecting photoelectric conversion device 66 is arranged at a position corresponding to a scanning start position on the packaged printed circuit board to detect the scanning start position and may be constructed of, for example, a photodiode. An I/V conversion circuit 67 converts a current signal produced from the scanning start position detecting photoelectric conversion device 66 into a voltage signal, and a comparator 68 compares the signal produced from the I/V conversion circuit 67 with a reference voltage 69 to convert it into a digital signal of "0" or "1". The measuring system excepting the polygon mirror 3 and polygon motor 4 in the construction of FIG. 1 is designated by reference numeral 70.

The operation of the jitter corrector for the polygon mirror constructed as above will be described. A fine light beam generated from the light source 56 is converted by the collimator lens system 57 into a parallel light flux which in turn is collected by the collecting lens system 58 into a fine light spot to be collected on the scanning line 59. The polygon mirror 3 is driven for rotation by the polygon motor 4 and the polygon mirror in rotation deflects the fine light beam having passed through the collecting lens system 58 to scan it on the scanning line 59 in a direction of arrow x.

As the polygon mirror 3 rotates, the fine light beam sequentially scans the photoelectric conversion devices 61 and 66 arranged on the scanning line 59, starting with the initial impingement on the scanning start position detecting photoelectric conversion device 66. A current signal delivered out of the scanning start position detecting photoelectric conversion device 66 is converted by the I/V conversion circuit 67 into a voltage signal which in turn is compared with the reference voltage 69 by means of the comparator 68. The comparator 68 delivers a digital signal which is "0" if the voltage signal is smaller than the reference voltage 69 but "1" if larger. This digital signal serves as a scanning start signal b.

Subsequently, as the polygon mirror 3 rotates, the fine light spot impinges on the rotation angle detecting photoelectric conversion devices 61 sequentially. The slit 60 disposed in front of the rotation angle detecting photoelectric conversion device 61 is adapted to sharpen the rising edge when the rotation angle detecting photoelectric conversion device 61 receives the fine light spot. When receiving the fine light spot, the rotation angle detecting photoelectric conversion device 61 generates a current signal, so that each time the polygon mirror 3 makes a rotation of a constant angle, a current signal is produced from each rotation angle detecting photoelectric conversion device 61. The current signal is converted by the I/V conversion circuit 62 into a voltage signal which in turn is compared with the reference voltage 64 by means of the comparator 63. The comparator 63 delivers a digital signal which is "0" if the voltage signal is smaller than the reference voltage 64 but "1" if larger. Digital signals are ORed by the OR circuit 81 to produce a rotation angle signal c. In other words, the rotation angle signal c is formed of a digital signal "1" delivered out of the OR circuit 81 when any one of the rotation angle detecting photoelectric conversion devices 61 receives the fine light spot and a digital signal "0" delivered out of the OR circuit 81 when none of the rotation angle detecting photoelectric conversion devices 61 receive the fine light spot. The polygon motor 4 delivers a z-phase signal a indicative of the origin of rotation angle every revolution.

Figure 19:
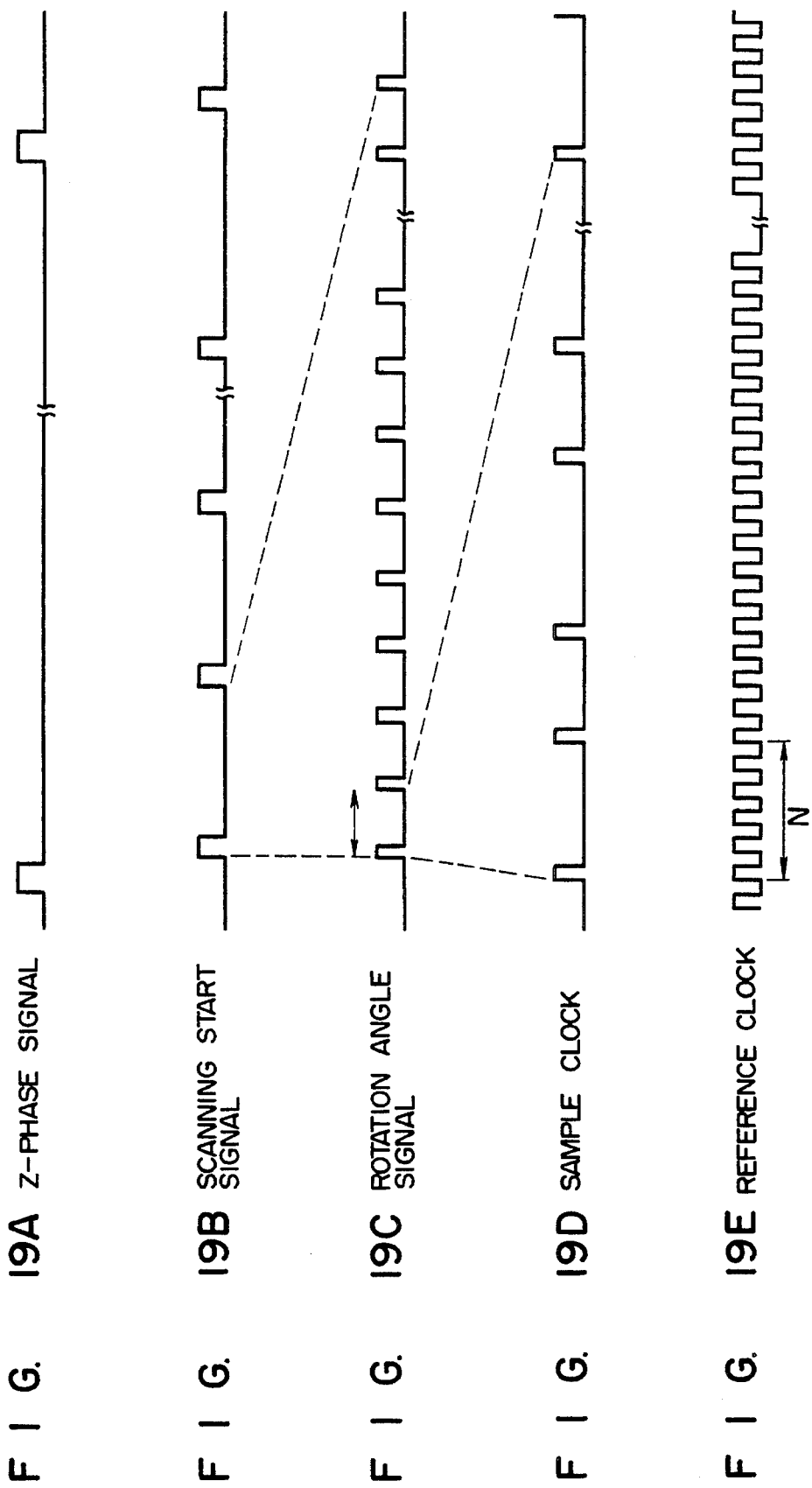
FIGS. 19A to 19E are timing charts for the jitter corrector of FIG. 18.

The z-phase signal a, scanning start signal b and rotation angle signal c delivered out of the above devices are mutually related as shown in FIG. 19. Firstly, one pulse of z-phase signal a is delivered each time the polygon mirror makes one revolution. The origin of rotation angle is defined by this signal. As the polygon mirror 3 subsequently rotates, one pulse of scanning start signal b is delivered at each reflection surface. Since in the present embodiment the number of surfaces of the polygon mirror is six, six pulses are delivered when the polygon mirror makes one revolution. While scanning on one line is effected by one surface of the polygon mirror, a rotation angle signal c is produced each time that the polygon mirror is rotated by a predetermined angle and therefore, the same number of pulses as that of the rotation angle detecting photoelectric conversion devices 61 can be obtained in respect of one surface of the polygon mirror. Here, the interval between adjacent pulses of rotation angle signal c is called a block.

At the time that scanning of one line ends and scanning of the next line starts, that is, scanning by the next refection surface is started, a second scanning start signal b is produced similarly and a rotation angle signal c is produced. In this manner, as the rotation of the polygon mirror 3 proceeds, the occurrence of these signals is repeated and a z-phase signal a occurs when one revolution ends. Each block is divided by sample clocks d to be described later and the interval between adjacent sample blocks d is determined by the sample interval clock number of a reference clock e.

Figure 20:
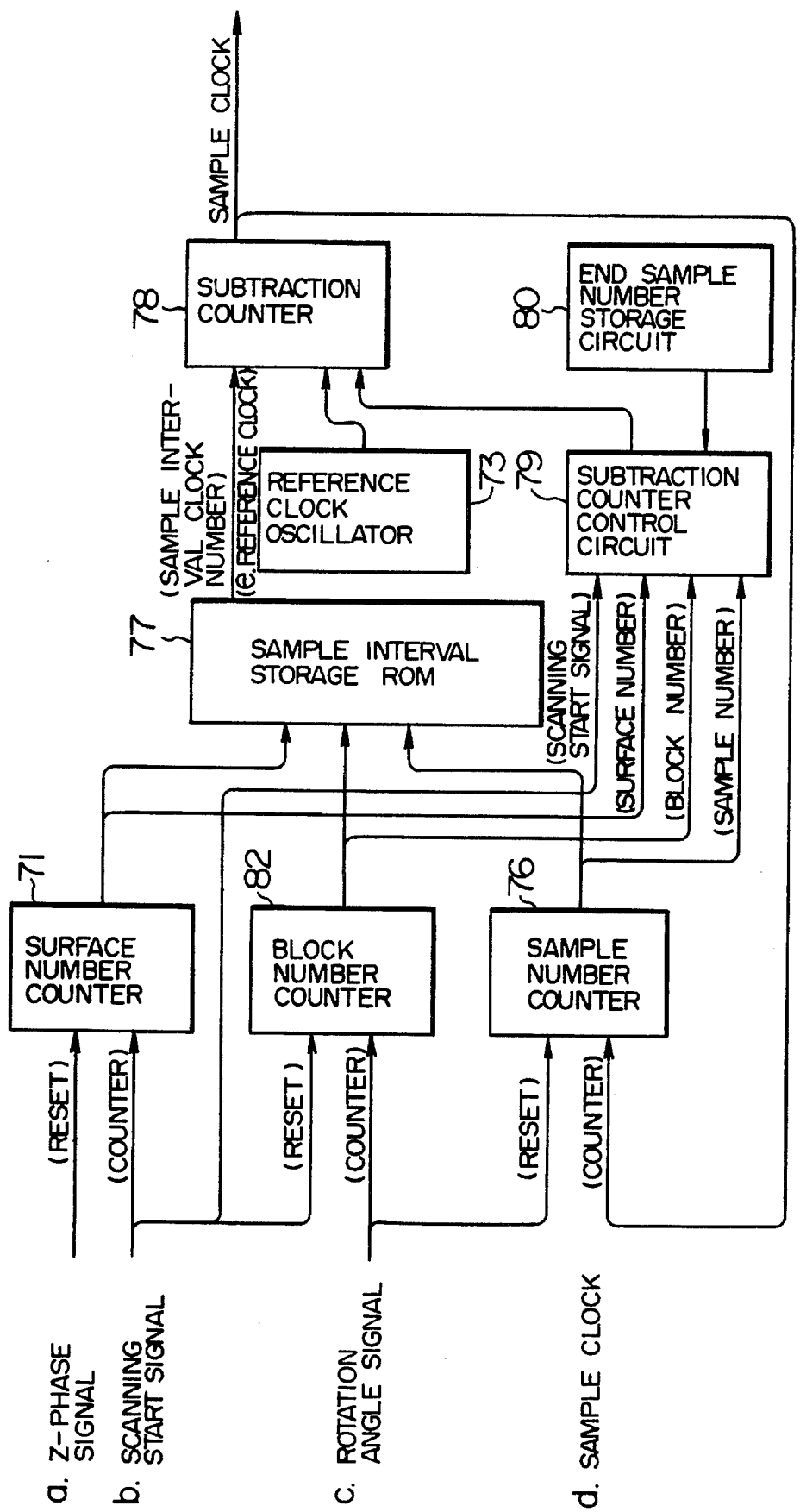
FIG. 20 is a block diagram of the jitter corrector of FIG. 18.

A circuit for generating a sample clock for measurement by using these signals is illustrated in FIG. 20. When one sample clock is generated, the scanning coordinate position is incremented by one and height measurement is commanded.

Firstly, a z-phase signal a resets the value of a surface number counter 71 indicating a reflection surface of the polygon mirror 71 to zero, and a scanning start signal b adds one to the value of the surface number counter 71. Thus, the surface number counter 71 delivers a number of a reflection surface of polygon mirror which is used for scanning presently.

Also, the scanning start signal b sets the value of a block number counter 82 indicating a block number during scanning to zero, and the value of the block number counter 82 is added with one each time a rotation angle signal c is inputted. Thus, the block number counter 82 delivers a block number which is under scanning presently.

Also, the rotation angle signal c resets the value of a sample number counter 76 to zero, and the value of the sample number counter 76 is added with one each time that a sample clock is inputted. Thus, the sample number counter 76 delivers a signal indicating what number of sample block (scanning coordinate position) the sample block has advanced to.

A sample interval storage ROM 77 records in advance a time interval between time for measuring a certain coordinate position and time for measuring the next coordinate position and when receiving a coordinate number, the sample interval storage ROM 77 delivers a time up to the next coordinate position. Here, the coordinate number is represented by the sum of surface number, block number and sample number and the time up to measurement at the next coordinate position is represented by the number of reference clocks of the reference clock oscillator 73 (sample interval clock number N). Thus, when receiving, as an address, the surface number, block number and sample number, the sample interval storage ROM 77 delivers a sample interval clock number up to the next sample clock.

The sample interval clock number delivered out of the sample interval storage ROM 77 is inputted to a succeeding stage of subtraction counter 78. In the subtraction counter 78, one is subtracted from the value of the sample interval clock number each time that one pulse of reference clock from a reference clock oscillator 73 is inputted and when a resulting value becomes zero, a sample clock is delivered as a borrow signal to command measurement. The sample clock is then inputted to the sample number counter 76.

The operation of the subtraction counter 78 is controlled by a subtraction counter control circuit 79. When receiving a scanning start signal b, the subtraction counter control circuit 79 delivers an operation start signal to the subtraction counter 78 to command it to start operation. An end sample number storage circuit 80 is written with an end sample number in a final block number in respect of each polygon mirror reflection surface and the value of the end sample number storage circuit 80 is compared with the surface number, block number and sample number which are inputted to the subtraction counter control circuit 79. When coincidence occurs therebetween in respect of each surface, an operation end signal is delivered to the subtraction counter 78 and the operation thereof is stopped. Thus, outside the scanning range, the operation of the subtraction counter 78 is stopped to stop the generation of the sample clock.

As described above, by providing the jitter corrector in the packaged printed circuit board inspection apparatus of FIG. 1 and generating sample clocks at time intervals complying with a rotation speed of the polygon mirror, accurate height data at scanning coordinate positions can always be acquired without being affected by irregularity in rotation of the polygon mirror.

Figure 21:
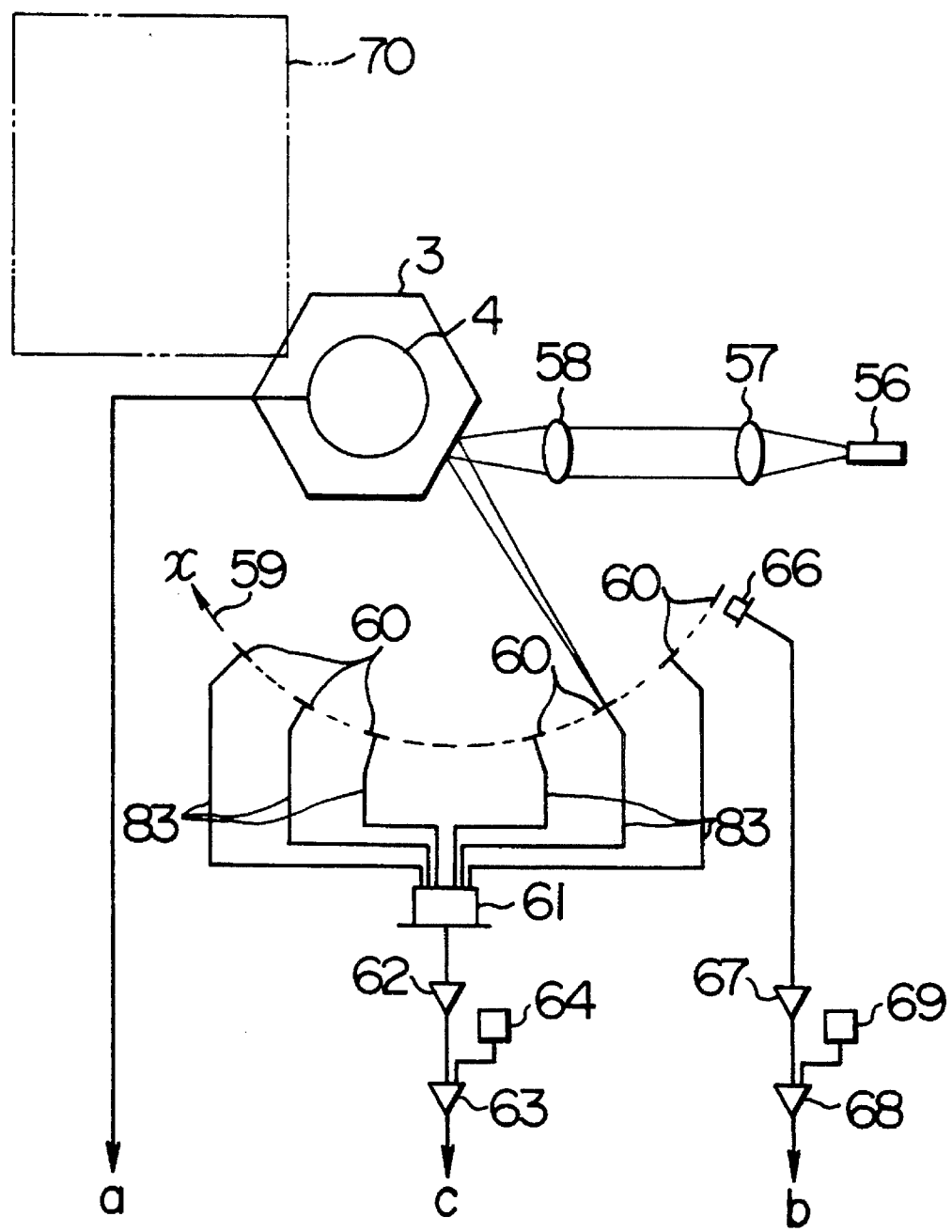
FIG. 21 is a diagram showing the construction of still another embodiment of the jitter corrector.

FIG. 21 shows the construction of still another embodiment of the jitter corrector which differs from the foregoing constructions in that optical fiber devices 83 are arranged at scanning positions in place of the photodiodes so that light beams may be guided to a photodiode. By virtue of the use of the optical fiber devices, a single photodiode, a single I/V conversion circuit and a single comparator can suffice.

Figure 22:
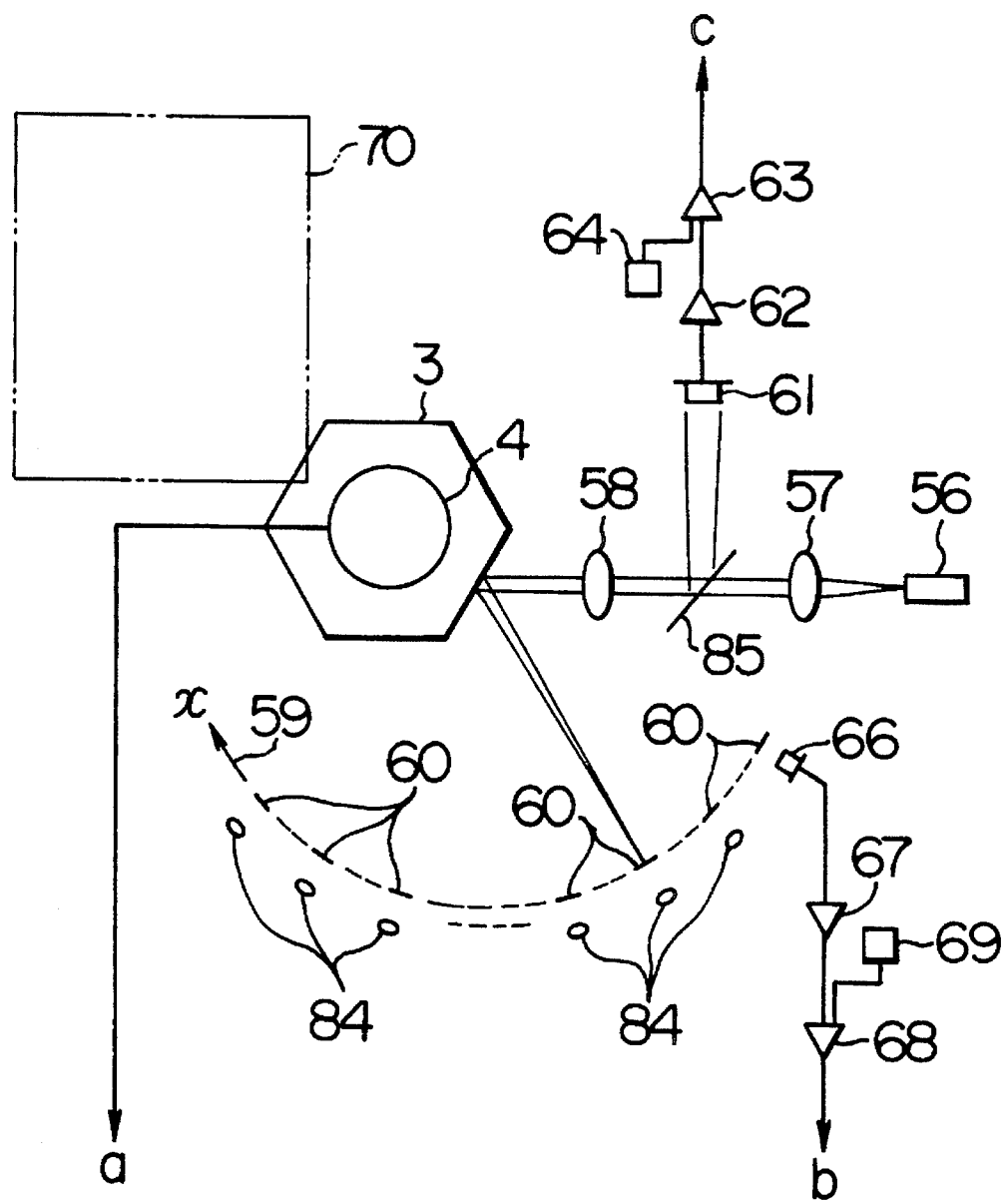
FIG. 22 is a diagram showing the construction of still another embodiment of the jitter corrector.

FIG. 22 shows the construction of still another embodiment of the jitter corrector for polygon mirror which differs from the foregoing constructions in that reflectors 84 are arranged at scanning positions in place of the photodiodes. The reflector 84 such as a mirror is so arranged as to have such a reflection angle that when the reflector 84 receives a fine light beam, a reflection beam from the reflector goes along a path reverse to that of the fine light beam and impinges on the polygon mirror. Accordingly, the instant that the fine light beam scans the reflector 84, the reflection beam of the fine light beam takes the reverse path to that of the fine light beam and it is deflected by the polygon mirror 3 and is again deflected by a tunnel mirror 85 so as to be incident on a photodiode 61. By virtue of the use of the reflector, a single photodiode, a single current/voltage conversion circuit and a single comparator can suffice.

As described above, in the packaged printed circuit board inspection apparatus in which a fine light beam emitted from the first light source is scanned on the packaged printed circuit board by using the polygon mirror and reflection beams from the packaged printed circuit board are guided to the light receiving unit, the jitter correctors as shown in FIGS. 18 to 22 are provided wherein a fine light beam emitted from the second light source separate from the first light source is deflected by the polygon mirror and received by a plurality of light receiving means arranged on the scanning line of the fine light beam, and a signal commanding sampling of the surface shape of the board in accordance with the rotation speed is generated.

By generating a sample clock at time intervals complying with the rotation speed of the polygon mirror, accurate height data at scanning coordinate positions can always be acquired without being affected by irregularity in rotation of the polygon mirror.

Figure 23A:
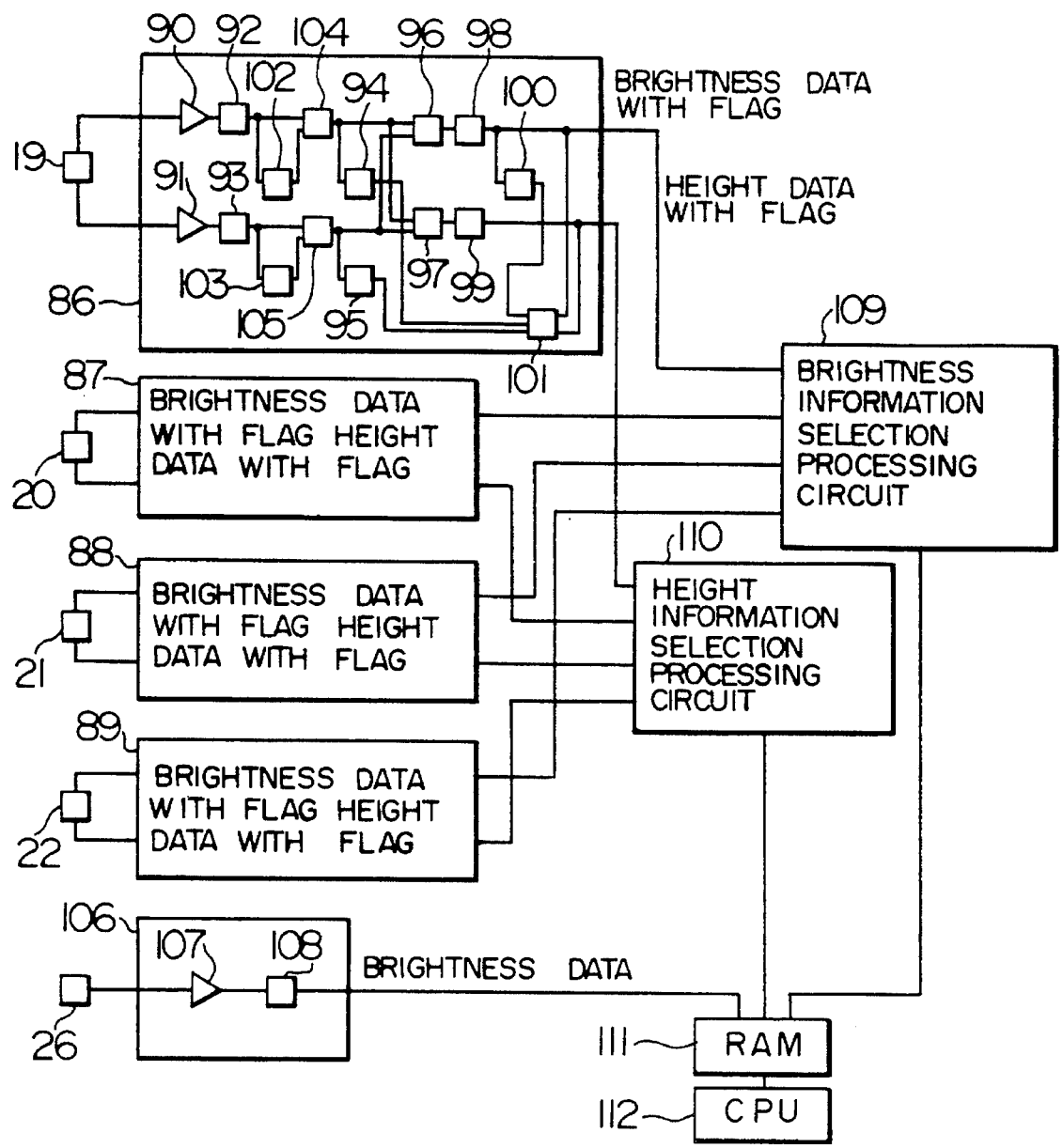
FIG. 23A is a block diagram showing an embodiment of an electric circuit of the packaged printed circuit board inspection apparatus according to the present invention.
Figure 23B:
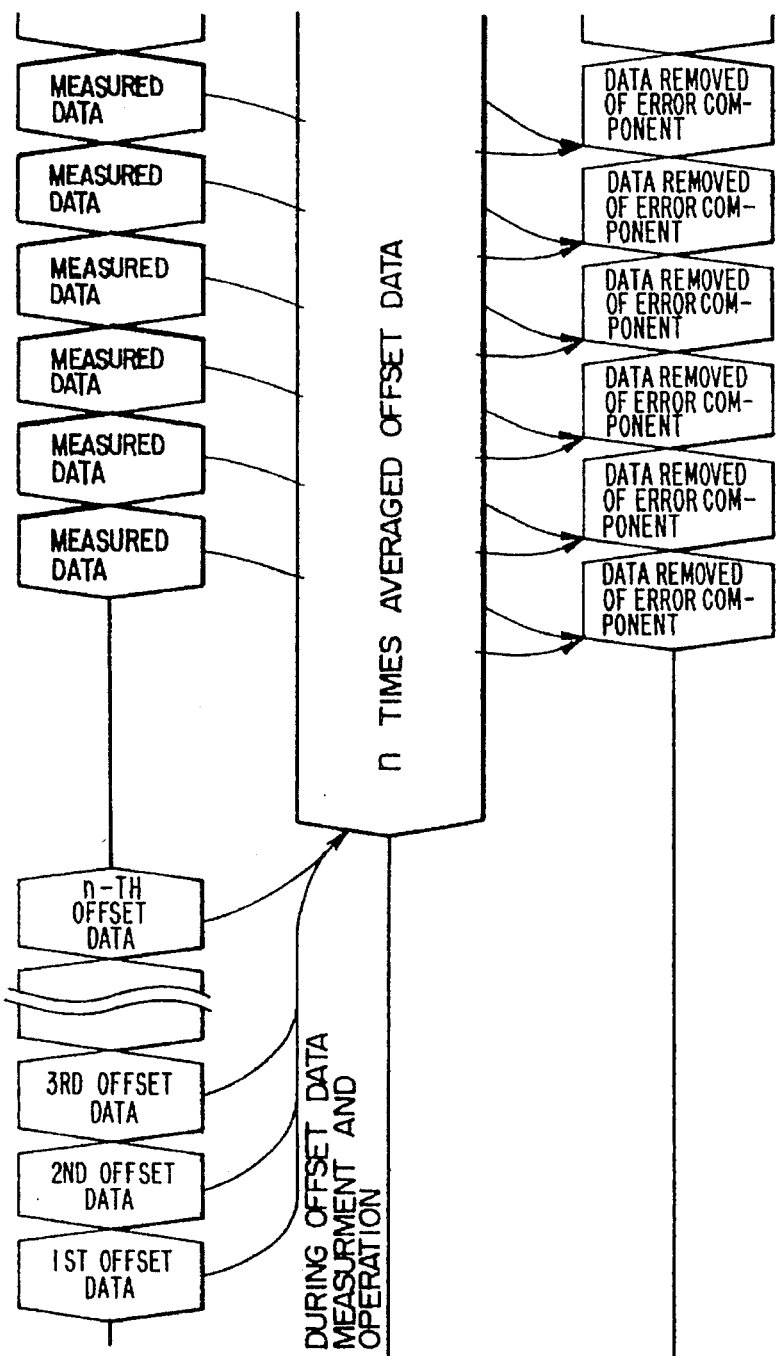
FIG. 23B is a diagram for explaining the operation of the electric circuit of FIG. 23A.

In the packaged printed circuit board inspection apparatus according to the invention as shown in FIG. 1 for inspecting the surface shape on the basis of height information and brightness information delivered out of the PSD's 19, 20, 21 and 22 and the photodiode 26, an electric circuit is employed which will be described hereunder. FIGS. 23A and 23B show an embodiment of the electric circuit according to the invention and its operation.

In FIGS. 23A and 23B, height/brightness operation circuits 86, 87, 88 and 89 determine brightness data with flag and height data with flag from outputs of the PSD's for measuring height data and brightness data. The height/brightness operation circuits 86, 87, 88 and 89 have the same construction, each including I/V conversion circuits 90 and 91 for converting currents from each PSD into voltages, A/D conversion circuits 92 and 93 for converting the analog voltages into digital values, comparator circuits 94, 95 and 100 for comparing input values with threshold values, an addition circuit 96 for adding digital values, a division circuit 97 for performing division of digital values, correction ROM's 98 and 99 for correcting digital values, and a flag calculation circuit 101 for calculating flags from outputs of the comparator circuits 94, 95 and 100. Offset average value operation/hold circuits 102 and 103 as well as subtraction circuits 104 and 105 are inserted between the A/D conversion circuits 92 and 93 and the addition circuit 96 and division circuit 97.

A brightness operation circuit 106 determines brightness data from an output of the photodiode 26. The brightness operation circuit 106 includes an I/V conversion circuit 107 and an A/D conversion circuit 108 for converting an analog voltage into a digital value.

The brightness data with flag and the height data with flag are sent to a brightness information selection processing circuit 109 and a height information selection processing circuit 110, respectively. Outputs from these circuits are applied, along with brightness data from the brightness operation circuit 106, to RAM 111 and CPU 112. The operation of the electric circuit constructed as above will be described. In the height/brightness operation circuits 86, 87, 88 and 89 associated with the PSD's 19, 20, 21 and 22, respectively, two current outputs from each PSD are converted by the I/V conversion circuits 90 and 91 into voltages which in turn are converted into digital values by the A/D conversion circuits 92 and 93. The digital output values are compared with threshold values (limit values capable of warranting the operation accuracy) by means of the comparator circuits 94 and 95 and comparison results are sent to the flag calculation circuit 101.

The two digital output values are on the one hand added together by means of the addition circuit 96 to provide brightness information at a fine light beam irradiation position and are on the other hand divided by each other by means of the division circuit 97 to provide height information at the fine light beam irradiation position. Output data of each of the addition circuit 96 and division circuit 97 (brightness information or height information) contains a measurement error (due to errors of individual optical systems and errors concomitant with the rotation of the polygon mirror) depending on the scanning position. To correct the above error, correction amounts at different scanning positions are measured in advance and recorded in the correction ROM's 98 and 99, and the output data of the addition circuit 96 and that of the division circuit 97 are corrected by making reference to the correction amounts. The brightness data having passed through the correction ROM 98 is compared with a certain threshold value (a limit value which permits the PSD to perform accurate measurement) by means of the comparator circuit 100, and a comparison result is sent to the flag calculation circuit 101. The flag calculation circuit 101 calculates the information from the comparator circuits 94, 95 and 100 to provide flags. The flags are added to the brightness data and the height data to provide brightness data with flag and height data with flag.

With this construction, four pieces of brightness data with flag and four pieces of height data in four directions can be obtained from one measuring point by means of the four height/brightness operation circuits 86, 87, 88 and 89. The brightness information selection processing circuit 109 performs a selection processing of the four pieces of brightness data with flag. For the selection processing, a method may be available wherein the maximum value of the four data pieces is determined. The height information selection processing circuit 110 performs a selection processing of the four pieces of height data with flag.

Available as a method for selection processing of the height data pieces is, for example, a method in which data pieces of flag information unwarrantable of measurement accuracy are removed and the remaining data pieces are averaged or a method, suitable for the case of the number of the remaining data pieces being large, in which data pieces of the maximum and minimum levels are removed and the remaining data pieces are averaged. The brightness information selection processing circuit 109 and the height information selection processing circuit 110 are provided for saving the RAM 111 and mitigating load on the CPU 112, and outputs of the selection processing circuits 109 and 110 are sent to the RAM 111 and CPU 112.

In the brightness operation circuit 106 associated with the photodiode 26, a current output from the photodiode is converted by the I/V conversion circuit 107 into a voltage which in turn is converted by the A/D conversion circuit 108 into a digital signal to be sent to the RAM 111. The photodiode 26 receiving a reflection beam vertically reflected from the packaged printed circuit board 6 delivers a large output when the inclination of a soldering surface is small or soldering is missed and the quantity of reflection beam in the vertical direction becomes large but conversely, it delivers a small output when the inclination of a soldering surface is large and the quantity of reflection beam becomes small. Therefore, when the outputs of the PSD's are small resulting in a failure to measure the height of a soldering surface correctly, the brightness information from the photodiode 26 can be referred to.

Then, the CPU 112 compares the height information and brightness information stored in the RAM 111 with reference height information and brightness information obtained in advance from the criterion of packaged printed circuit board and stored, thus inspecting the quality of a packaging state of the packaged printed circuit board.

In the above construction, however, an electric error occurs in an electric circuit between each of the PSD's and each of the A/D conversion circuits 92 and 93 and the influence of the error cannot be eliminated, with the result that the output of each of the height/brightness operation circuits 86, 87, 88 and 89 contains an error. To eliminate the electrical error component, in the electric circuit construction of the present embodiment, the offset average value operation/hold circuits 102 and 103 as well as subtraction circuits 104 and 105 are particularly added between the A/D conversion circuits 92 and 93 and the addition circuit 96 and division circuit 97.

The operation of the electric circuit will now be described with reference to FIG. 23B. Electrical error data signifies an output of the PSD produced when the PSD does not receive any reflection beam, that is, an output of the PSD which is produced owing to light beams other than reflection beams from the board, and measurement of the electrical error data is carried out by using an output of the PSD which is produced under the condition that no reflection beam is received from the packaged printed circuit board, i.e., when the light source 1 is turned off.

Firstly, the light source 1 is turned off before an inspection is started and under this condition, two electric signals indicative of electrical errors from the PSD 19 are converted into voltage signals by means of the I/V conversion circuits 90 and 91. The voltage signals are then converted into digital signals by means of the A/D conversion circuits 92 and 93. These signals are processed to provide a first offset data piece. The above measurement is repeated n times to prepare n offset data pieces. An offset average value is determined from these n offset data pieces by means of the offset average value operation/hold circuit and held therein as average offset data.

When the light source 1 is turned on and the inspection of the packaged printed circuit board is started, current outputs representative of measured data sampled at a plurality of positions on the scanning line, delivered out of the PSD 19 and containing electrical error components, are converted by the I/V conversion circuits 90 and 91 into voltage signals which in turn are converted by the A/D conversion circuits 92 and 93 into digital signals. Then, the average offset data pieces held in the offset average value operation/ hold circuits 102 and 103 are subtracted from the digital signals by means of the subtraction circuits 104 and 105 to remove the electrical error signals. Digital signals thus removed of the electrical error signals are inputted to the addition circuit 96 and the division circuit 97. The subsequent operation is similar to that of the electric circuit of embodiment 1.

While in the present embodiment the method of turning off the light source 1 is used as an example of realization of a state of no reflection beam from the packaged printed circuit board, electrical error data may be measured through a method of optically intercepting the light source 1 or a method in which the packaged printed circuit board is conditioned such that any reflective objects escape from the irradiation position.

Figure 24A:
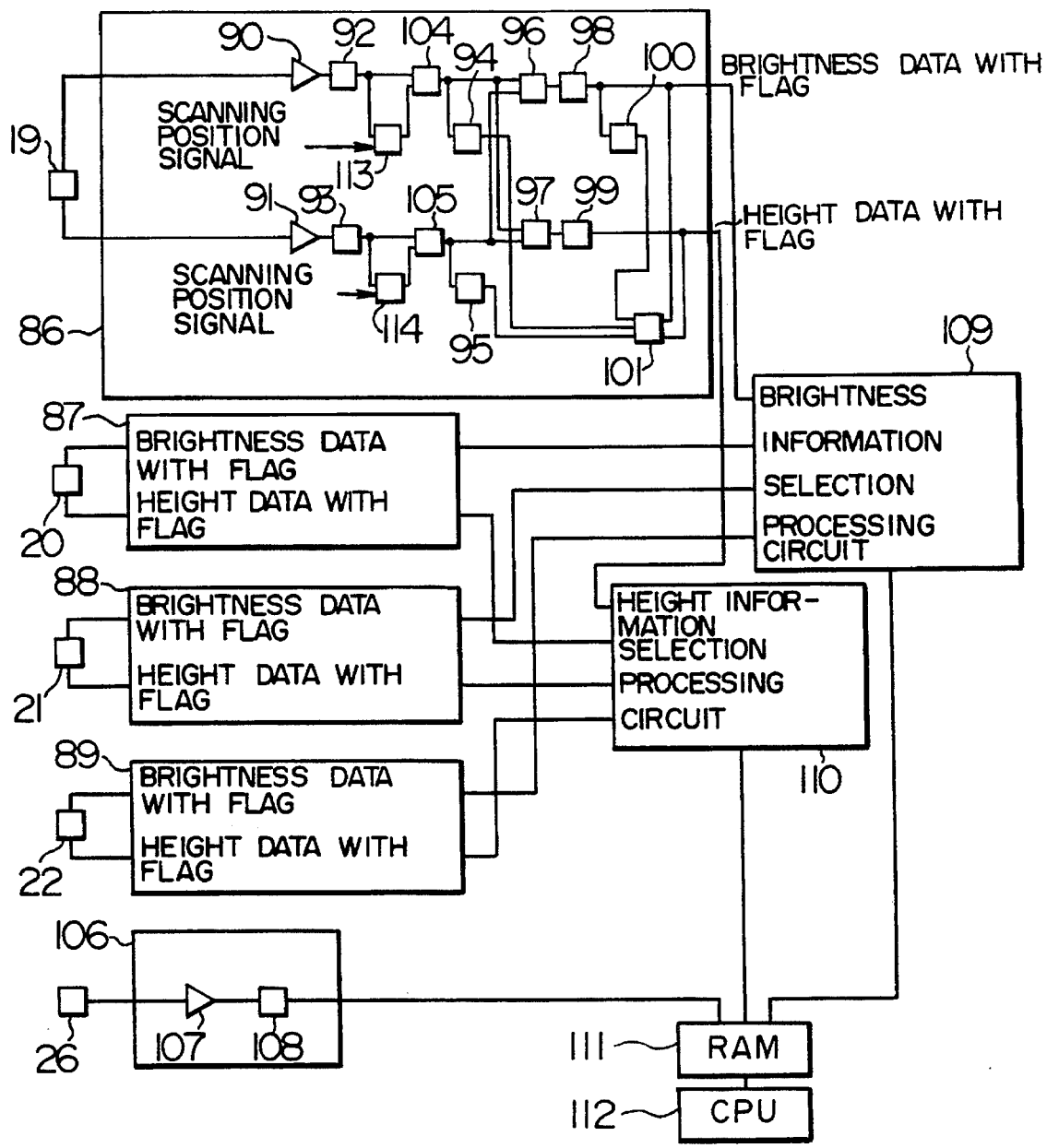
FIG. 24A is a block diagram showing another embodiment of the electric circuit.
Figure 24B:
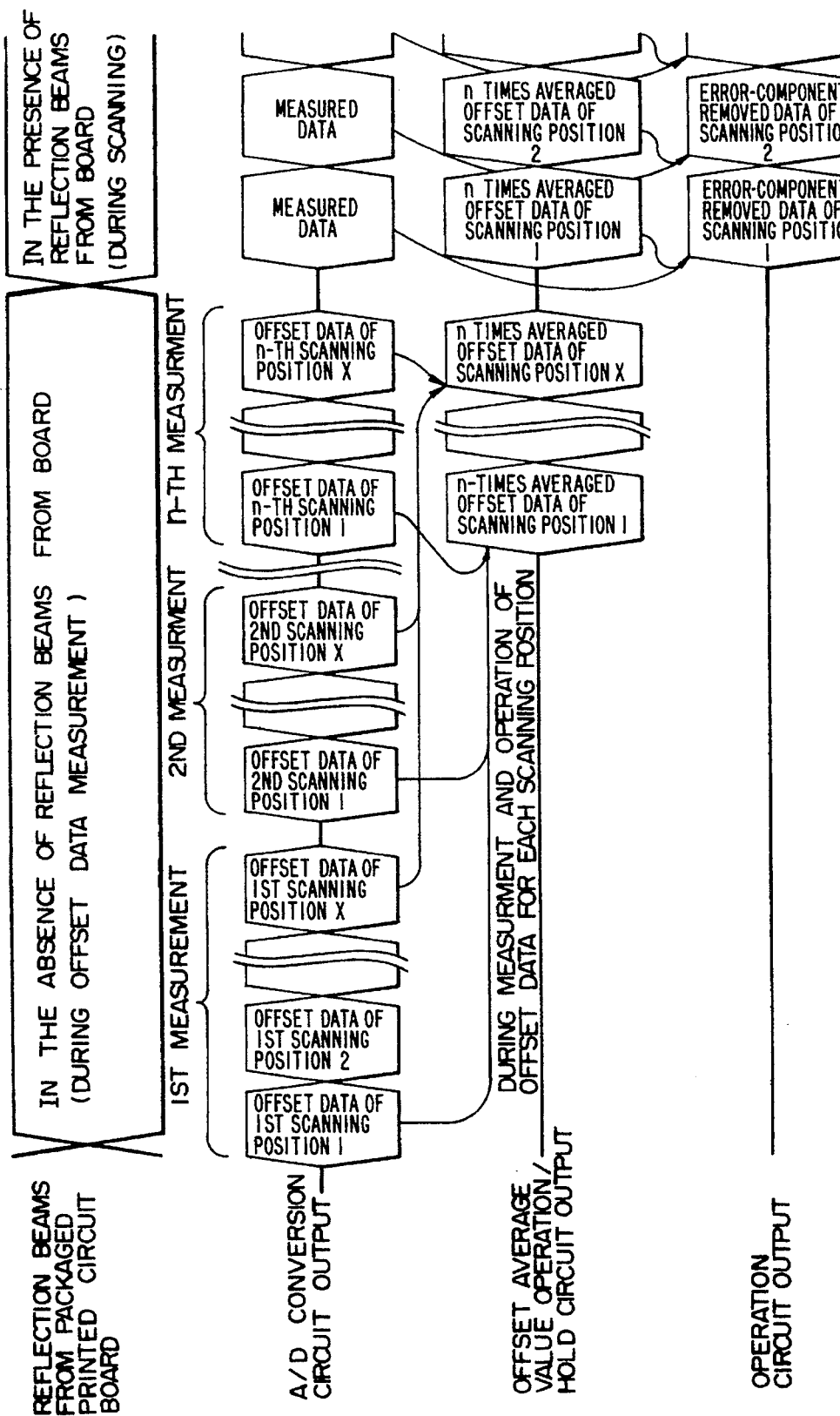
FIG. 24B is a diagram for explaining the operation of the electric circuit of FIG. 24A.
Figure 25:
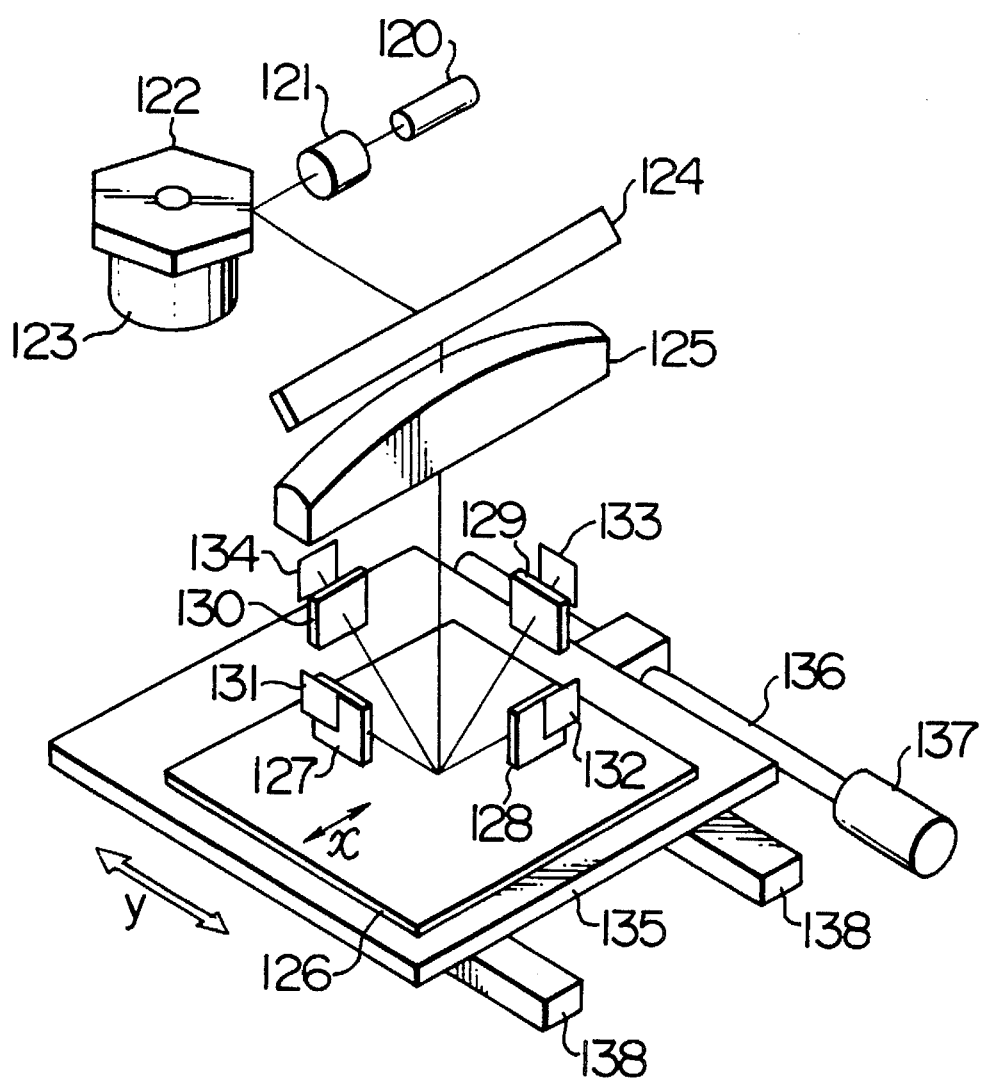
FIG. 25 is a perspective view showing an example of a conventional packaged printed circuit board inspection apparatus.
Figure 26:
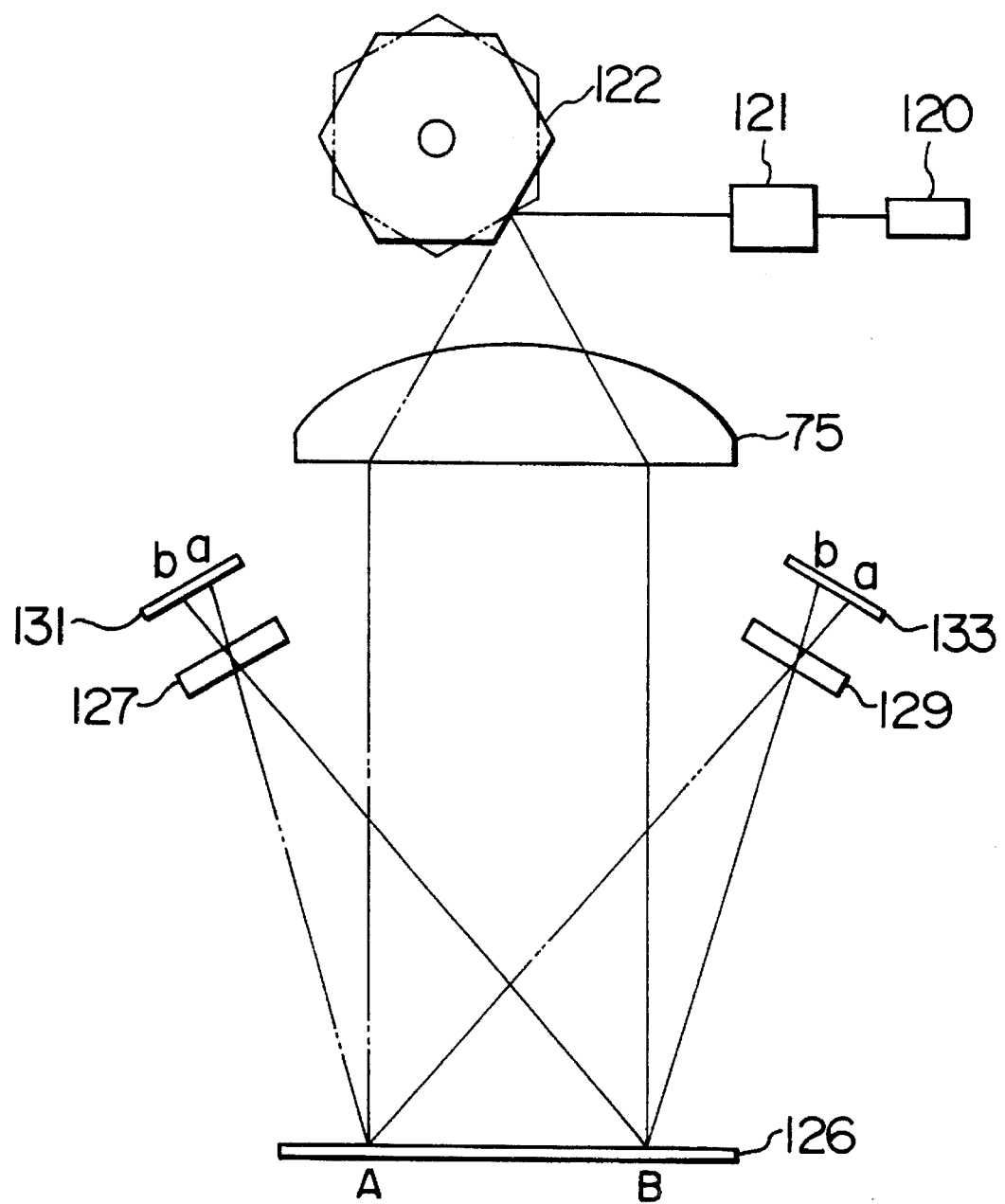
FIG. 26 is a side view of FIG. 25 as viewed in a direction of arrow y.

FIGS. 24A and 24B show another embodiment of the electric circuit according to the invention. FIG. 24A is an electric circuit diagram and FIG. 24B is an operation timing chart.

In the electric circuit construction of FIGS. 23A and 23B, the influence of the electrical error generated in the electric circuit between each of the PSD's 19, 20, 21 and 22 and each of the A/D conversion circuits 92 and 93 can be removed but optical errors which are different for different scanning positions cannot be removed. For example, optical errors result from the fact that a light beam emitted from the light source 1 is reflected at the surface of the light projection fθ lens 5 and the surface of the polygon mirror and reflection beams scattered from these surfaces impinge on the PSD's 19, 20, 21 and 22 and these optical errors cannot be eliminated.

Accordingly, in the electric circuit construction of FIGS. 24A and 24B, offset average value operation/hold circuits 113 and 114 and subtraction circuits 104 and 105 for each scanning position are added between the A/D conversion circuits 92 and 93 and the addition circuit 96 and division circuit 97 in order to remove the electrical error component and the optical error components for each scanning position.

The operation of the electric circuit block diagram of FIG. 24A will be described with reference to FIG. 24B. Before the packaged printed circuit board is actually scanned, electrical error data generated in the electric circuit and optical error data for each scanning position are measured. Firstly, the packaged printed circuit board is conditioned such that reflection beams are not generated therefrom, for example, the packaged printed circuit board escapes from the irradiation position and under this condition, the light source 1 is kept to be turned on. During the first scanning, current outputs representative of electrical errors and optical errors for individual scanning positions (scanning position 1 to scanning position x) which are produced from the PSD 19 are converted by the I/V conversion circuits 90 and 91 into voltage signals which in turn are converted by the A/D conversion circuits 92 and 93 to provide offset data. Through n scanning operations, n offset data pieces for respective scanning positions are prepared. Then, an average value of the n offset data pieces is determined for the individual scanning positions by means of the offset average value operation/hold circuits 113 and 114 to prepare average offset data pieces which in turn are stored therein.

When the packaged printed circuit board moves to the scanning position and an inspection is started, current outputs representative of measured data sampled at a plurality of positions on the scanning line, produced from the PSD 19 and containing the electrical error component and the optical error components, are converted by the I/V conversion circuits 90 and 91 into voltage signals which in turn are converted into digital signals by the A/D conversion circuits 92 and 93. Then, the average offset data pieces corresponding to scanning positions and held in the offset average value operation/hold circuits 113 and 114 are subtracted from the digital signals in respect of individual scanning positions by means of the subtraction circuits 104 and 105 to remove the electrical error and the optical error. Digital signals thus removed of the electrical error and the optical error are inputted to the addition circuit 96 and division circuit 97. The subsequent operation is similar to that of the foregoing embodiment.

While in the present embodiment the method is exemplified wherein the packaged printed circuit board escapes from the irradiation position so as to be conditioned such that reflection beams are not generated from the packaged printed circuit board, reflection beams can be prevented from impinging on the receiving light fθ lenses 11, 12, 13 and 14 through a method in which the light path is changed by a mirror immediately before the irradiation position on the packaged printed circuit board or a method in which the light path is intercepted by a light absorbing material.

As described above, according to the electric circuits of FIGS. 23A and 23B and FIGS. 24A and 24B, an electric circuit can be constructed wherein an electrical analog output of the photoelectric conversion device produced in compliance with its light receiving position for reflection beams from the board can be converted into a digital signal to provide board height data and brightness data, and in particular, an error can be eliminated which is caused when the photoelectric conversion device does not receive any reflection beams from the packaged printed circuit board to be inspected or which is caused by an output component of the photoelectric conversion device output which is generated even when no reflection beam is received.

In addition, the electric circuit can be constructed wherein by detecting an offset of the output of the PSD in respect of a plurality of measuring positions on each scanning line on the board, errors due to optical measuring units for the packaged printed circuit board can be removed in respect of individual measuring positions.

We claim:

1. An apparatus for inspection of a packaged printed circuit board, said apparatus comprising:

a light source for generating a light beam which is irradiated on a packaged printed circuit board to be inspected;

deflection means for deflecting said light beam generated from said light source to cause said light beam to scan said packaged printed circuit board;

a light projection lens system for irradiating said light beam deflected by said deflection means onto said packaged printed circuit board in a fixed direction such that said light beam is always parallel to said fixed direction when said light beam is incident on said packaged printed circuit board, reflection beams being scattered from said packaged printed circuit board from incident positions of said light beam on said packaged printed circuit board;

a plurality of optical path correcting means for receiving ones of said reflection beams having constant directional vectors relative to the fixed direction regardless of a change of the incident position of said light beam on said packaged printed circuit board and for guiding the received reflection beams such that said received reflection beams become parallel to said fixed direction;

a light receiving optical system for guiding a plurality of said reflection beams received by said plurality of optical path correcting means to said deflection means in parallel to each other; and photoelectric conversion means for receiving said reflection beams deflected by said deflection means and converting light quantities of the reflection beams received by said photoelectric conversion means into electrical outputs indicating respective heights of said light beam incident positions on said packaged printed circuit board.

2. An apparatus according to claim 1 wherein a polygon mirror is used as said deflection means.

3. An apparatus according to claim 2 wherein said polygon mirror is disposed such that its rotary shaft is normal to gravitation.

4. An apparatus according to claim 2 wherein a rotary shaft of said polygon mirror is offset.

5. An apparatus according to claim 2 wherein said light projection lens system or said light receiving lens system includes a fθ lens and a symmetrical axis of said fθ lens is offset in the scanning direction in accordance with an offset of said polygon mirror.

6. An apparatus according to claim 1 wherein said optical path correcting means includes a prism adapted to deflect said reflection beams to the fixed direction.

7. An apparatus according to claim 1 wherein said optical path correcting means makes constant optical paths of said reflection beams extending from said packaged printed circuit board to said light receiving lens system regardless of the change of the incident position.

8. An apparatus according to claim 1 wherein said optical path correcting means includes a cylindrical lens for collecting light beams in the fixed direction.

9. An apparatus according to claim 6 wherein a phenomenon that the incident position of said reflection beams on said light receiving lens system is shifted in a direction normal to the scanning direction by the change of the scanning position is corrected by rotating said cylindrical lens about its optical axis.

10. An apparatus according to claim 1 wherein said light beam emitted from said light source is reflected at said deflection means at an angle which is acute.

11. An apparatus according to claim 1 wherein said light projection lens system and said light receiving lens system are formed of a unitary fθ lens.

12. An apparatus according to claim 1 wherein said light projection lens system or said light receiving lens system is formed of a cylindrical fθ lens.

13. An apparatus according to claim 1 wherein an acousto-optical device (AO device) is arranged on an optical path of said reflection beams between said deflection means and said photoelectric conversion means, for correcting an optical path of said reflection beams incident on said photoelectric conversion means in accordance with the incident position of said light beam on said packaged printed circuit board.

14. An apparatus according to claim 1 wherein said photoelectric conversion means is moved for correcting an optical path of said reflection beams incident on said photoelectric conversion means in accordance with the incident position of said light beam on said packaged printed circuit board.

15. An apparatus according to claim 1 wherein said light projection lens system and said light receiving lens system include fθ lenses of mutually different focal lengths, respectively.

16. An apparatus according to claim 1, wherein said photoelectric conversion means includes a photodiode divided to produce electrical outputs independent of each other.

17. An apparatus according to claim 1, wherein said light receiving optical system further comprises a cylindrical lens having a flattened surface through which said light beam output by said light projection lens system passes, said cylindrical lens being interposed between said light projection lens system and said packaged printed circuit board to collect ones of said reflection beams reflected in the fixed direction.

18. An apparatus according to claim 1, wherein said deflection means comprises a polygon mirror and said apparatus further comprises:

a light projection unit for irradiating a second light beam onto said polygon mirror and collecting said second light beam;

second photoelectric conversion means, arranged on a scanning line on which said second light beam deflected by said polygon mirror and emitted from said light projection unit is collected, to produce an electrical output in respect of each surface of said polygon mirror; and circuit means for detecting a rotating time of each surface of said polygon mirror on the basis of the electrical outputs of said second photoelectric conversion means to detect a rotation speed of said polygon mirror and for preparing, at a timing complying with the rotation speed, a signal which commands the detection of said reflection beams from said packaged printed circuit board.

19. An apparatus according to claim 1, wherein said deflection means comprises a polygon mirror and said apparatus further comprises:

a light projection unit for irradiating a second light beam onto said polygon mirror and collecting said second light beam;

second photoelectric conversion means, arranged on a scanning line on which said second light beam deflected by said polygon mirror and emitted from said light projection unit is collected, to produce electrical outputs on the basis of which rotational positions of said polygon mirror are detected; and circuit means, responsive to the electrical outputs of said second photoelectric conversion means and reference clock signals delivered at a shorter interval than said output signals, for producing a signal indicative of a timing for detection of said reflection beams from said packaged printed circuit board.

20. An apparatus according to claim 19 wherein said second photoelectric conversion means comprises:

a plurality of optical fiber devices arranged at a plurality of positions on the scanning line on which said second light beam emitted from said light projection unit is collected; and a photoelectric conversion device for receiving light outputs of said plurality of optical fiber devices and converting said light outputs into said electrical outputs so as to detect said rotational positions of said polygon mirror.

21. An apparatus according to claim 19 wherein said second photoelectric conversion means comprises:

reflectors arranged at a plurality of positions on the scanning line on which said light beam emitted from said light projection unit is collected; and a photoelectric conversion device for receiving a component of said second light beam returning from said reflectors which is further reflected by said deflection means, so as to detect said rotational positions of said polygon mirror.

22. An apparatus according to claim 1, wherein:

said photoelectric conversion means produces said electrical outputs as electrical analog signals; and said apparatus further comprises:

analog/digital conversion means for converting the electrical analog signals from said photoelectric conversion means into digital signals, determining output values produced from said photoelectric conversion means when said light beam is not scanned on said packaged printed circuit board, subtracting said output values from said digital signals produced by said analog/digital conversion means when said packaged printed circuit board is scanned to produce differences, and outputting said differences; and height/brightness operation means for calculating height data and brightness data of said packaged printed circuit board in accordance with said differences.

23. An apparatus according to claim 22 wherein said output values produced from said photoelectric conversion means when said reflection beams of said light beam do not exist in respect of a plurality of mutually different measuring positions for inspection of a surface shape of said packaged printed circuit board are determined by said analog/digital conversion means in respect of each scanning line of said light beam on said packaged printed circuit board, said output values calculated in respect of said measuring positions are respectively subtracted from respective ones of said digital signals of said analog/digital conversion means produced in respect of individual ones of said measuring positions when said packaged printed circuit board is scanned to produce said differences, and said differences are delivered to said height/brightness operation means.

24. An apparatus according to claim 1, wherein said constant directional vectors comprise at least four different directional vectors.

25. An apparatus according to claim 1, wherein said photoelectric conversion means comprises a photodiode and a tunnel mirror, disposed in a path of the light beam generated by the light source, for transmitting the light beam generated by the light source to the deflection means and for reflecting a portion of one of said reflection beams deflected by said deflection means onto said photodiode.

* * * * *